United States Patent
Raslambekov

(10) Patent No.: US 11,833,759 B1
(45) Date of Patent: Dec. 5, 2023

(54) SYSTEMS AND METHODS FOR MAKING AN ORTHODONTIC APPLIANCE

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 17/944,180

(22) Filed: Sep. 13, 2022

(51) Int. Cl.
| | |
|---|---|
| B29C 64/386 | (2017.01) |
| A61C 13/34 | (2006.01) |
| B33Y 80/00 | (2015.01) |
| A61C 7/08 | (2006.01) |
| B33Y 50/00 | (2015.01) |
| A61C 7/00 | (2006.01) |

(52) U.S. Cl.
CPC ............ B29C 64/386 (2017.08); A61C 7/002 (2013.01); A61C 7/08 (2013.01); A61C 13/34 (2013.01); B33Y 50/00 (2014.12); B33Y 80/00 (2014.12)

(58) Field of Classification Search
CPC ......... B29C 64/386; A61C 7/002; A61C 7/08; A61C 13/34; B33Y 50/00; B33Y 80/00
See application file for complete search history.

(56) References Cited

U.S. PATENT DOCUMENTS

| | | |
|---|---|---|
| 10,856,954 B1 | 12/2020 | Raslambekov |
| 10,993,782 B1 | 5/2021 | Raslambekov |
| 11,033,362 B2 | 6/2021 | Matov et al. |
| 11,055,850 B1 | 7/2021 | Raslambekov |
| 11,191,618 B1 | 12/2021 | Raslambekov |
| 11,191,619 B1 | 12/2021 | Raslambekov |
| 11,259,897 B1 | 3/2022 | Raslambekov |
| 11,364,103 B1 | 6/2022 | Raslambekov |
| 2002/0006217 A1* | 1/2002 | Rubbert ................. A61C 7/146 382/154 |
| 2018/0333231 A1* | 11/2018 | Somasundaram ..... A61C 19/05 |
| 2023/0035538 A1* | 2/2023 | Marshall .............. A61C 9/0053 |

OTHER PUBLICATIONS

U.S. Appl. No. 16/704,718, filed Dec. 5, 2019.

* cited by examiner

*Primary Examiner* — Bijan Mapar
(74) *Attorney, Agent, or Firm* — BCF LLP

(57) ABSTRACT

A method and a system for making an orthodontic appliance are provided, the method comprises: obtaining a 3D digital model comprising a plurality of vertices representative of surfaces of upper and lower teeth of a subject in a current occlusion therebetween; obtaining an indication of a desired occlusion between the upper and lower arch forms; determining, based on the desired occlusion, a shift value between the current occlusion and the desired occlusion; generating, based on the desired occlusion, an outer surface of the appliance 3D digital model corresponds to the respective occlusal surface portion of the given one of the upper and lower teeth having been repositioned towards the desired occlusion by the shift value.

17 Claims, 16 Drawing Sheets

SYSTEMS AND METHODS FOR MAKING AN ORTHODONTIC APPLIANCE

FIELD

The present technology relates generally to systems and methods for producing an orthodontic appliance for a subject.

BACKGROUND

In orthodontics, treating orthodontic disorders of a subject may include applying a number of consecutive treatment steps in which orthodontic appliances, such as orthodontic aligners, are consecutively used to apply forces onto at least some of a subject's teeth to cause movement of the subject's teeth towards their respective desired positions, typically associated with alignment of the subject's teeth or normal occlusion thereof.

Some of the orthodontic disorders can include bite malocclusions, such as an overbite, for example, where teeth of an upper arch form of the subject abnormally protrude forward over the teeth of a lower arch form. Another example of a bite malocclusion includes an underbite where, in contrast to the overbite, the teeth of the lower arch form protrude beyond the teeth of the upper arch form. Treatments of such orthodontic conditions can include repositioning and further retaining the lower arch form relative to the upper arch form in a desired position, associated with the normal occlusion between the teeth.

In one example, retaining the lower arch form relative to the upper arch form in the desired position can include applying a specific orthodontic appliance, such as an orthodontic elastic, which when attached to the teeth of the upper and lower arch forms (such as via hooks or attachments), can be configured to apply to the lower arch form a certain amount of elastic force, thereby bringing the lower arch form in the desired position relative to the upper arch form.

In another example, the retaining can be executed by adding to the orthodontic aligners applied to the teeth of the upper and lower arch forms certain additional elements, configured to engage with each other, such as indents and protrusions configured to interlock therebetween, in the desired position of the lower arch form relative to the upper arch form.

However, such additional elements used in these approaches for retaining the lower arch form in the desired position, as not forming part of the subject's intraoral anatomy, may cause discomfort to the subject, which can thus affect the subject's adherence to the orthodontic treatment, and hence effectiveness of the entire orthodontic treatment.

Certain prior art approaches have been proposed to tackle the above-identified technical problem.

U.S. Pat. No. 11,033,362-B2, issued on Jun. 15, 2021, assigned to Align Technology Inc, and entitled "GENERATING A DYNAMIC THREE-DIMENSIONAL OCCLUSOGRAM", discloses methods and systems for generating a three-dimensional occlusogram. One method includes determining a virtual three-dimensional (3D) mesh model object of at least one tooth of a patient and displaying the determined virtual 3D mesh model object of at least one tooth of a patient wherein the 3D mesh model object includes a plurality of data sets associated with a set of occlusal information for the at least one tooth of the patient.

SUMMARY

Developers of the present technology have appreciated that positioning and further retaining the lower arch form in the desired position can be achieved by modelling, for example, on surfaces of orthodontic appliances to be applied to the teeth, an occlusal surface of at least one of the lower and upper teeth of the subject corresponding to a desired occlusion therebetween. More specifically, the present methods and systems disclosed herein are directed to making an orthodontic aligner whose outer surface reproduces surfaces of a given one of the lower and upper teeth in the desired occlusion therebetween. To that end, non-limiting embodiments of the present technology are directed to shifting, on the outer surface of the orthodontic aligner, current occlusal surfaces of the given one of the upper and lower teeth towards the desired occlusion therebetween. However, at the same time, the inner surface of the orthodontic aligner may be configured to cause the given one of the lower and upper teeth towards their target positions, typically associated with their alignment.

In at least some non-limiting embodiments of the present technology, an amount of shift applied to the current occlusion within the outer surface of the orthodontic appliance can be divided among a plurality of orthodontic aligners applied during the course of the orthodontic treatment, causing the lower arch form to gradually progress to the desired position during the orthodontic treatment, corresponding to the desired occlusion between the lower and upper teeth of the subject.

Thus, the present methods are directed to determining a configuration of the orthodontic aligner, which, when applied to the subject's teeth, is configured to reposition and retain the lower teeth in the desired position relative to the upper teeth, and, having a more anatomically shaped outer surface. This provides for an improved wear comfort of such an orthodontic aligner and can thus help increase subject's adherence to the orthodontic treatment.

More specifically, in accordance with a first broad aspect of the present technology, there is provided a method for making an orthodontic appliance for a subject. The method is executable by a processor of a computer system. The method comprises: obtaining, by the processor, a 3D digital model comprising a plurality of vertices representative of surfaces of an upper arch form and a lower arch form of the subject, the upper arch form including upper teeth and the lower arch form including lower teeth, each one of the upper teeth and the lower teeth having a respective occlusal surface portion defining a current occlusion therebetween; obtaining, by the processor, an indication of a desired occlusion between the upper and lower arch forms; determining, by the processor, based on the desired occlusion, a shift value between the current occlusion and the desired occlusion; generating, by the processor, based on the desired occlusion, an appliance 3D digital model of the orthodontic appliance, such that an outer surface of the appliance 3D digital model corresponds to the respective occlusal surface portion of the given one of the upper and lower teeth having been repositioned towards the desired occlusion by the shift value; and storing, by the processor, in a database of the computer system, the generated appliance 3D digital model.

In some implementations of the method, the generating comprises: determining, by the processor, using the 3D digital model, an occlusal surface 3D digital model representative of a topography of the current occlusion between the upper arch form and the lower arch form, the occlusal surface 3D digital model having at least one occlusal surface landmark aligning with one or both of: a corresponding upper teeth landmark in the respective occlusal surface portion of the upper teeth and a lower teeth landmark in the respective occlusal surface portion of the lower teeth; applying, by the processor, in the 3D digital model, the occlusal surface 3D digital model to one or both of the respective occlusal surface portions of the upper teeth and the respective occlusal surface portion of the lower teeth, the applying comprising: positioning, in the 3D digital model, the occlusal surface 3D digital model on one of (i) the respective occlusal surface portion of the upper teeth such that the landmark aligns with the upper teeth landmark, and (ii) the respective occlusal surface portion of the lower teeth such that the landmark aligns with the lower teeth landmark; and moving the occlusal surface 3D digital model towards the desired occlusion; and generating, by the processor, the appliance 3D digital model based on the 3D digital model with the occlusal surface 3D digital model applied thereon.

In some implementations of the method, the determining, by the processor, the shift value comprises obtaining data indicative of the current occlusion and the desired occlusion of the upper arch form and the lower arch form, and identifying a distance value, along a translational direction, between the current occlusion and the desired occlusion.

In some implementations of the method, the translational direction is determined along an occlusal plane between the upper and lower teeth.

In some implementations of the method, the method further comprises generating, based on the shift value, a plurality of shift intervals, and wherein the moving the occlusal surface 3D digital model by the shift value comprises moving the occlusal surface 3D digital model by a given one of the shift intervals.

In some implementations of the method, the orthodontic appliance is a one of a plurality of orthodontic appliances to be applied to the subject during an orthodontic treatment, a given one of the plurality of orthodontic appliances being determined based on a respective appliance 3D digital model with the occlusal surface 3D digital model being moved to a respective one of the plurality of shift intervals.

In some implementations of the method, each one of the plurality of shift intervals is predetermined.

In some implementations of the method, each one of the plurality of shift intervals is equal.

In some implementations of the method, the determining the occlusal surface 3D digital model comprises: identifying, in the respective occlusal surface of one of the upper teeth and the lower teeth of the 3D digital model, at least one vertex representative of the current occlusion; identifying, in the other of the upper teeth and the lower teeth of the 3D digital model, a corresponding vertex, forming a pair of vertices; applying a predetermined rule to all of the identified pairs of vertices to generate the occlusal surface 3D digital model.

In some implementations of the method, the identifying the at least one vertex representative of the current occlusion comprises: positioning an occlusal plane between the upper teeth and the lower teeth; and translating vertices from the occlusal plane to one of the upper teeth and the lower teeth, and determining the translated vertices as the at least one vertex representative of the current occlusion.

In some implementations of the method, the translating the vertices comprises moving the vertices along normal vectors from the occlusal plane towards the one of the upper teeth and the lower teeth.

In some implementations of the method, the predetermined rule comprises identifying an occlusal surface vertex as a vertex which is a predetermined distance between the vertices of the identified pair of vertices.

In some implementations of the method, the corresponding vertex is identified by extending a line from the at least one vertex of the upper teeth or the lower teeth towards the other of the upper teeth or the lower teeth.

In some implementations of the method, the line is defined as one of: (i) extending parallel to an axis of a given tooth associated with the at least one vertex, (ii) extending along a movement trajectory of the upper arch form relative to the lower arch form when moving from the current occlusion to the desired occlusion, and (iii) extending along a normal vector to a surface of the given tooth associated with the at least one vertex.

In some implementations of the method, the method further comprises identifying vertices in which a distance between the pair of vertices is greater than a predetermined distance threshold value, and removing the vertices in which a distance between the pair of vertices is greater than a predetermined distance threshold value from the one of the occlusal surface of the upper teeth and the occlusal surface of the lower teeth of the 3D digital model.

In some implementations of the method, the method further comprises smoothing the occlusal surface 3D digital model.

In some implementations of the method, the method further comprises causing, by the processor, manufacture of the orthodontic appliance based on the appliance 3D digital model.

In some implementations of the method, the manufacture of the orthodontic appliance is by additive manufacturing, and the causing comprises sending instructions to an additive manufacturing system.

In some implementations of the method, the manufacture of the orthodontic appliance is by thermoforming, and the causing comprises sending instructions to a thermoforming system.

In some implementations of the method, the orthodontic appliance is an orthodontic aligner.

In some implementations of the method, the generating comprises: obtaining a raw appliance 3D digital model having been determined based on the 3D digital model such that: both an inner surface and an outer surface of the raw appliance 3D digital model correspond to the respective occlusal surface portion of the given one of the upper and lower teeth in the current occlusion therebetween; determining, by the processor, using the 3D digital model, an occlusal surface 3D digital model representative of a topography of the current occlusion between the upper arch form and the lower arch form, the occlusal surface 3D digital model having at least one occlusal surface landmark aligning with one or both of: a corresponding upper teeth landmark in the respective occlusal surface portion of the upper teeth and a lower teeth landmark in the respective occlusal surface portion of the lower teeth; applying, by the processor, to the outer surface of the raw appliance 3D digital model, the occlusal surface 3D digital model, the applying comprising: positioning, in the raw appliance 3D digital model, the occlusal surface 3D digital model on the respective occlusal surface portion of the given one of the upper teeth and the lower teeth such that the corresponding landmark aligns with a respective one of the upper teeth landmark and the lower teeth landmark; and moving the occlusal surface 3D digital model towards the desired occlusion; and determining, by the processor, the appliance 3D digital model as being the raw appliance 3D digital model with the occlusal surface 3D digital model applied thereon.

In accordance with a second broad aspect of the present technology, there is provided a method for making an orthodontic appliance for a subject. The method is executable by a processor of a computer system. The method comprises: obtaining, by the processor, a 3D digital model comprising a plurality of vertices representative of surfaces of an upper arch form and a lower arch form of the subject, the upper arch form including upper teeth and the lower arch form including lower teeth, each one of the upper teeth and the lower teeth having a respective occlusal surface portion defining a current occlusion therebetween; obtaining, by the processor, an indication of a desired occlusion between the upper and lower arch forms; determining, by the processor, based on the desired occlusion, a shift value between the current occlusion and the desired occlusion; generating, by the processor, based on the desired occlusion, an appliance 3D digital model of the orthodontic appliance, such that: an inner surface of the appliance 3D digital model corresponds to the respective occlusal surface portion of a given one of the upper and lower teeth in the current occlusion therebetween; and an outer surface of the appliance 3D digital model corresponds to the respective occlusal surface portion of the given one of the upper and lower teeth having been repositioned towards the desired occlusion by the shift value; and storing, by the processor, in a database of the computer system, the generated appliance 3D digital model.

In accordance with a third broad aspect of the present technology, there is provided a method for making an orthodontic appliance for a subject. The method is executable by a processor of a computer system. The method comprises: obtaining a raw appliance 3D digital model which has been determined such that: both an inner surface and an outer surface of the raw appliance 3D digital model correspond to a respective occlusal surface portion of the given one of the upper and lower teeth in a current occlusion therebetween; obtaining, by the processor, an occlusal surface 3D digital model representative of a topography of the current occlusion between the upper arch form and the lower arch form, the occlusal surface 3D digital model having at least one occlusal surface landmark aligning with one or both of: a corresponding upper teeth landmark in the respective occlusal surface portion of the upper teeth and a lower teeth landmark in the respective occlusal surface portion of the lower teeth; obtaining, by the processor, an indication of a desired occlusion between the upper and teeth; determining, by the processor, based on the desired occlusion, a shift value between the current occlusion and the desired occlusion; applying, by the processor, to the outer surface of the raw appliance 3D digital model, the occlusal surface 3D digital model, the applying comprising: positioning, in the raw appliance 3D digital model, the occlusal surface 3D digital model on the respective occlusal surface portion of the given one of the upper teeth and the lower teeth such that the corresponding landmark aligns with a respective one of the upper teeth landmark and the lower teeth landmark; and moving the occlusal surface 3D digital model towards the desired occlusion; determining, by the processor, the appliance 3D digital model as being the raw appliance 3D digital model with the occlusal surface 3D digital model applied thereon; and storing, by the processor, in a database of the computer system, the determined appliance 3D digital model.

In accordance with a fourth broad aspect of the present technology, there is provided a system for making an orthodontic appliance for a subject. The system comprises a processor and a non-transitory computer-readable medium storing instructions. The processor, upon executing the instructions, is configured to: obtain a 3D digital model comprising a plurality of vertices representative of surfaces of an upper arch form and a lower arch form of the subject, the upper arch form including upper teeth and the lower arch form including lower teeth, each one of the upper teeth and the lower teeth having a respective occlusal surface portion defining a current occlusion therebetween; obtain an indication of a desired occlusion between the upper and lower arch forms; determine, based on the desired occlusion, a shift value between the current occlusion and the desired occlusion; generate, based on the desired occlusion, an appliance 3D digital model of the orthodontic appliance, such that an outer surface of the appliance 3D digital model corresponds to the respective occlusal surface portion of the given one of the upper and lower teeth having been repositioned towards the desired occlusion by the shift value; and store, in the non-transitory computer-readable medium, the generated appliance 3D digital model.

In accordance with a fifth broad aspect of the present technology, there is provided a system for making an orthodontic appliance for a subject. The system comprises a processor and a non-transitory computer-readable medium storing instructions. The processor, upon executing the instructions, is configured to: obtain a 3D digital model comprising a plurality of vertices representative of surfaces of an upper arch form and a lower arch form of the subject, the upper arch form including upper teeth and the lower arch form including lower teeth, each one of the upper teeth and the lower teeth having a respective occlusal surface portion defining a current occlusion therebetween; obtain an indication of a desired occlusion between the upper and lower arch forms; determine, based on the desired occlusion, a shift value between the current occlusion and the desired occlusion; generate, based on the desired occlusion, an appliance 3D digital model of the orthodontic appliance, such that: an inner surface of the appliance 3D digital model corresponds to the respective occlusal surface portion of a given one of the upper and lower teeth in the current occlusion therebetween; and an outer surface of the appliance 3D digital model corresponds to the respective occlusal surface portion of the given one of the upper and lower teeth having been repositioned towards the desired occlusion by the shift value; and store, in the non-transitory computer-readable medium, the generated appliance 3D digital model.

In the context of the present specification, unless expressly provided otherwise, the term "orthodontic treatment" is broadly referred to as any type of medical intervention aimed at correcting malocclusions associated with the teeth or jaw of the subject, or moving the subject's teeth or jaws for any reason, including surgical and non-surgical manipulations, such as, but not limited to, using one or more of aligners, brackets, multi-strand wires, strips, retainers, and plates. Further, the orthodontic treatment, as referred to herein, may be determined automatically by a software, based on image data and other inputs associated with the subject, or semi-automatically with input from a practitioner in the field of dentistry (such as an orthodontist, a maxillofacial surgeon, for example).

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid-state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects, and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

Certain aspects and embodiments of the present technology are directed to methods of and systems for determining a shape of an orthodontic appliance, such as an orthodontic aligner, configured to reposition the lower arch form to a desired position relative to the upper arch form of the subject.

More specifically, certain aspects and embodiments of the present technology comprise a computer-implemented method of determining a configuration of the orthodontic appliance, whose outer surface is representative of a desired occlusion between the lower and upper teeth of the subject. In other words, at least some non-limiting embodiments of the present technology are directed to shifting, within the outer surface of the orthodontic appliance, occlusal surfaces of a given one of the upper and lower teeth towards the desired occlusion. By doing so, the lower arch form can be retained in the desired positioned relative to the upper arch form. However, an inner surface of the orthodontic appliance can be determined as being configured to receive the given one of the upper teeth and the lower teeth of the subject and cause individual movements thereof towards their predetermined target positions.

Certain embodiments of the present technology minimize, reduce or avoid some of the problems noted with the prior art. For example, implementing certain embodiments of the present technology, may allow increasing effectiveness of the orthodontic treatment including application of the above-mentioned orthodontic appliances.

More specifically, the increased effectiveness can be attained by determining the orthodontic appliance having, compared to the prior art approaches noted above, a more anatomically shaped outer surface, which would provide for a better wear comfort of the orthodontic appliance during the orthodontic treatment. This may thus increase the subject's adherence to the orthodontic treatment, which may further translate to an increased overall effectiveness thereof.

Orthodontic Treatment

Figure 1A:
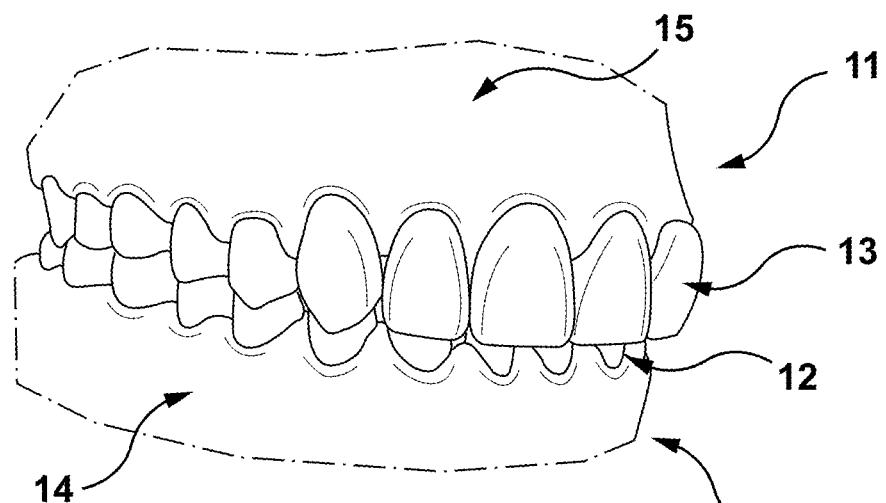
FIGS. 1A and 1B depict perspective views of lower and upper arch forms of a subject depicting respective examples of malocclusions of subject's teeth, in accordance with certain non-limiting embodiments of the present technology.
Figure 1B:
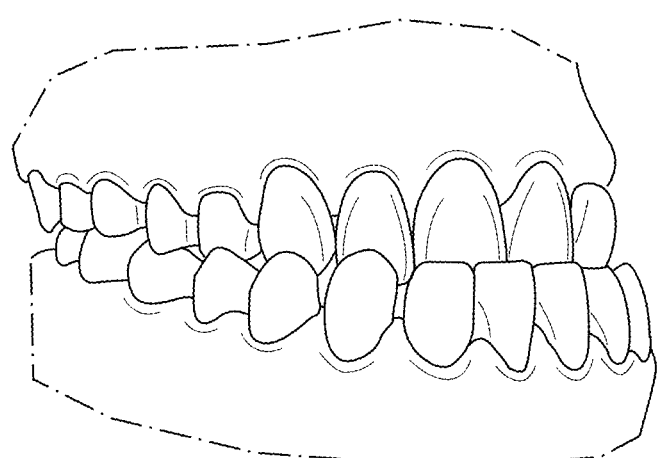

With initial reference to FIGS. 1A and 1B, there are depicted perspective views of a lower arch form 10 and an upper arch form 11 of the subject (also referred to herein as "patient", not depicted) illustrating examples of malocclusions therebetween, to which certain aspects and non-limiting embodiments of the present technology may be applied. The lower arch form 10 includes lower teeth 12 and a lower gingiva 14; and the upper arch form 11 includes upper teeth 13 and an upper gingiva 15.

Figure 1C:
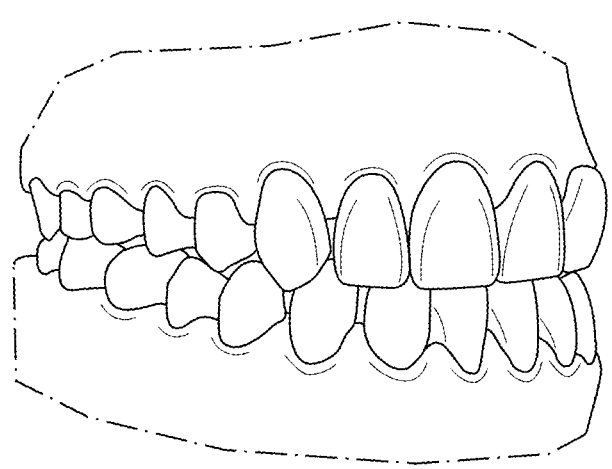
FIG. 1C depicts a perspective view of the lower and upper arch forms of the subject corresponding to the normal occlusion between the subject's teeth, in accordance with certain non-limiting embodiments of the present technology.

In the context of the present technology, the term "malocclusion" denotes an irregular spatial relationship between the lower teeth 12 and the upper teeth 13, deviated from a normal occlusion, such as that schematically depicted in FIG. 1C, in accordance with certain non-limiting embodiments of the present technology. More specifically, in certain embodiments, the normal occlusion between the lower and upper teeth 12, 13 is a state when both the lower and upper teeth 12, 13 are aligned within the lower and upper arch forms 10, 11, respectively, and when a mesiobuccal cusp of an upper first molar (not separately labelled) of the upper teeth 13 is received in a buccal groove of a lower first molar (not separately labelled) of the lower teeth 12.

According to certain non-limiting embodiments of the present technology, one example of the malocclusion between the lower and upper teeth 12, 13 of the subject includes an overbite, as schematically depicted in FIG. 1A. As best seen from FIG. 1A, the overbite occurs when the upper teeth 13 abnormally protrude beyond the lower teeth 13. Another example of the malocclusion can include an underbite, as schematically depicted in FIG. 1B. As it can be appreciated, in contrast with the overbite, the underbite is characterized by an abnormal protrusion of the lower teeth 12 beyond the upper teeth 13.

Other examples (not depicted) of the malocclusion between the lower and upper teeth 12, 13 of the subject, according to certain non-limiting embodiments of the present technology, may include, without limitation: an overjet, an underjet, different configurations of crossbites, an open bite, crowding of some of the lower teeth 12 and the upper teeth 13, midline shift therebetween, and others.

In some non-limiting embodiments of the present technology, for resolving the above-mentioned malocclusions, an orthodontic treatment may be provided to the subject.

In some non-limiting embodiments of the present technology, the orthodontic treatment may comprise applying an orthodontic appliance to at least one of the lower and upper arch forms 10, 11 of the subject. Generally speaking, the orthodontic appliance can be configured to cause the lower arch form 10 to displace from a current position, corresponding to one of the malocclusions as depicted in one of the FIGS. 1A and 1B, to a desired position relative to the upper arch form 11, where occlusal surfaces of at least some of the lower and upper teeth 12, 13, such as first molars or anterior teeth, for example, form a desired occlusion, such as the normal occlusion depicted in FIG. 1C. Further, in some non-limiting embodiments of the present technology, concurrently with the retaining the lower arch form 10 in the desired position relative to the upper arch form 11, the same or other orthodontic appliance can be used to reposition the lower or upper teeth 12, 13 to their target positions, which, for example, can be associated with their alignment within the lower and upper arch form 10, 11, respectively, and hence the desired occlusion therebetween.

Returning to the example of the overbite described above with reference to FIG. 1A, a first orthodontic appliance can be applied to at least one of the lower and upper arch forms 10, 11 to cause a movement of the lower arch form 10, as a whole, such that (i) anterior lower teeth (not separately labelled) of the lower teeth 12 move downwards from behind anterior upper teeth (not separately labelled) of the upper teeth 13; and (ii) the at least some of the lower and upper teeth 12, 13 form the desired occlusion therebetween, allowing other ones of the lower teeth and upper teeth 12, 13 to move towards the desired occlusion. At the same time, a second orthodontic appliance can be applied to cause movement of the lower teeth 12 towards the desired occlusion. More specifically, the second orthodontic appliance can be configured to (i) intrude the anterior lower teeth (not separately labelled) in the lower gingiva 14; (ii) cause tipping of the anterior lower teeth (also known as proclination); and/or (iii) cause expansion of posterior lower teeth (not separately labelled) of the lower teeth 12. By doing so, the second orthodontic appliance can be configured to cause movement of the lower teeth 12 such that the contact area therebetween and the upper teeth 13 corresponds to the desired occlusion.

In the example of the underbite, the first orthodontic appliance can be applied to at least one of the lower and upper arch forms 10, 11 to cause a movement of the lower arch form 10, as a whole, such that (i) the anterior lower teeth (not separately labelled) of the lower teeth 12 move downwards from over the anterior upper teeth (not separately labelled) of the upper teeth 13; and (ii) the at least some of the lower and upper teeth 12, 13 form the desired occlusion therebetween allowing other ones of the lower teeth and upper teeth 12, 13 to move towards the desired occlusion. Further, the second orthodontic appliance can be applied to the upper teeth 13 to cause: (i) extrusion of the anterior upper teeth of the upper teeth 13 from the upper gingiva 15; (ii) tipping of the anterior upper teeth; and (iii) and/or expansion of posterior upper teeth of the upper teeth 13 until the contact area between the lower and the upper teeth 12, 13 corresponds to the desired occlusion therebetween.

In some non-limiting embodiments of the present technology, the first orthodontic appliance can comprise at least one of a bite splint, a bite plate, or bite ramps, configured to bring the lower arch form 10 in the desired occlusion with the upper arch form 11. In other non-limiting embodiments of the present technology, the first orthodontic appliance can include an orthodontic elastic attached to the lower and upper arch forms 10, 11, such as by means of specific attachments or hooks, for example, attached to the some of the lower and upper teeth 12, 13. The orthodontic elastic can be produced from a shape-memory polymer material having a predetermined elasticity modulus and is thus configured to exert a force onto the lower arch form 10 causing it to reposition and be retained in the desired position relative to the upper arch form 11. In yet other non-limiting embodiments of the present technology, the first orthodontic appliance can comprise a Herbst appliance made of material, such as a metal, configured to rigidly retain the lower arch form in the desired position relative to the upper arch form along a bite trajectory.

Further, according to certain non-limiting embodiments of the present technology, the second orthodontic appliance can comprise orthodontic appliances of different types, shapes, sizes and configurations causing individual ones of the lower and upper teeth 12, 13 to move to their target positions. For example, the second orthodontic appliance can include, without limitation, aligners, brackets, multi-strand wires, strips, retainers, and plates. In a specific non-limiting example, the second orthodontic appliance may include a bracket system including: (i) brackets to be attached to at least some of the lower teeth 12 and/or the upper teeth 13; and (ii) a wire typically produced from a shape memory alloy, such as Nitinol, as an example, that is received in the brackets of the at least some of the lower teeth 12 and/or the upper teeth 13.

In other words, the first orthodontic appliance can be configured to retain the desired relative position between the lower and upper arch forms 10, 11, to which the second orthodontic appliance can be configured to adjust individual positions of the lower and upper teeth 12, 13 such that they form the desired occlusion.

In the non-limiting embodiments of the present technology, a single orthodontic appliance can be used for both (i) repositioning the lower arch form 10 to the desired position relative to the upper arch form 11; and (ii) causing movement of the at least some of the lower and upper teeth 12, 13 to their respective target positions where the desired occlusion occurs therebetween. According to certain non-limiting embodiments of the present technology, the single orthodontic appliance comprises at least one orthodontic aligner with a modified outer surface.

Figure 2A:
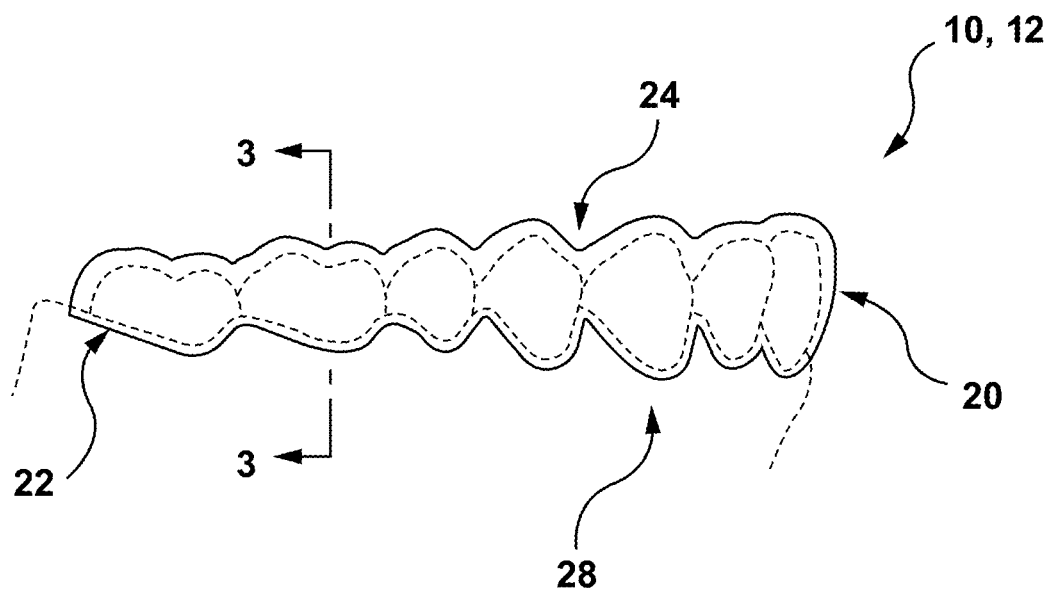
FIGS. 2A and 2B depict a side view and a cross-sectional view through line 3-3, respectively, of an orthodontic appliance applied to the subject's teeth that may be configured to treat the malocclusions of the subject's teeth present in FIG. 1, in accordance with certain non-limiting embodiments of the present technology.
Figure 2B:
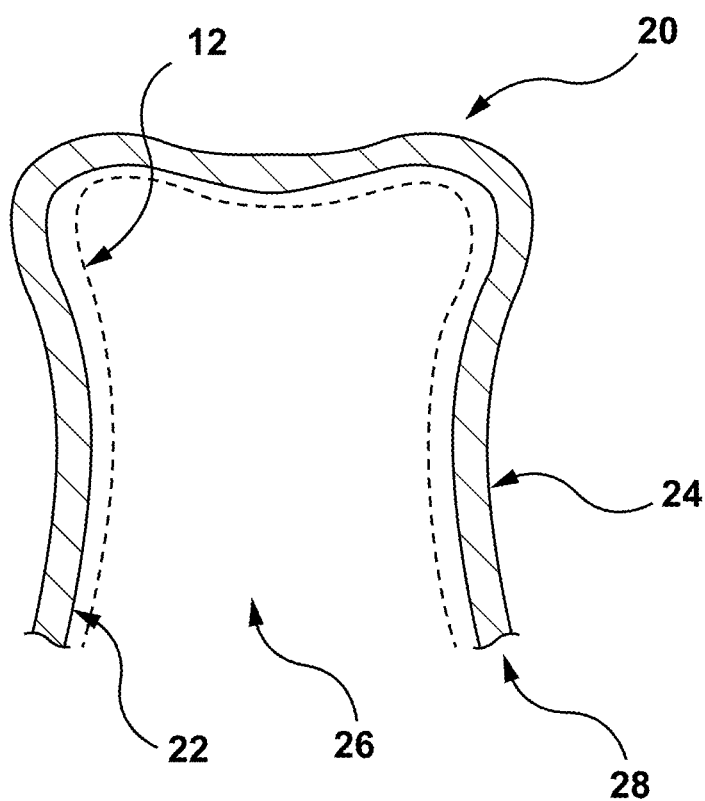

With reference to FIGS. 2A and 2B, there is depicted an aligner 20 applied to at least some of the lower teeth 12, in accordance with certain non-limiting embodiments of the present technology. The aligner 20 comprises an inner surface 22 and an outer surface 24. The inner surface 22 defines a channel 26, which is configured, in some non-limiting embodiments of the present technology, for receiving crown portions, for example, of at least some of the lower teeth 12. However, in other non-limiting embodiments of the present technology, the channel 26 of the aligner 20 may be configured to receive crown portions of all of the lower teeth 12. At least one edge, such as a front edge 28 (also referred to herein as an "open edge"), of the channel 26 is shaped for following a gum line (not separately numbered) along the lower gingiva 14.

It will be appreciated that, in accordance with certain non-limiting embodiments of the present technology, the aligner 20 may be used for treating different teeth malocclusions, including but not limited to one or more of: closing interdental spaces ("space closure"), creating/widening interdental spaces, tooth rotation, tooth tipping, tooth intrusion/extrusion, and tooth translation, to name a few. It should further be noted that in certain non-limiting embodiments of the present technology, applying the aligner 20 to the lower teeth 12 may further include applying specific attachments thereto.

As may become apparent, the aligner 20 may be designed in such a way that its inner surface 22 is configured to impose respective forces on one or more of the lower teeth 12 to obtain a desired position of the lower teeth 12 at a given stage of the orthodontic treatment.

Needless to say, although in the depicted embodiments of FIGS. 2A and 2B, the aligner 20 is configured to be applied onto the lower teeth 12, in other non-limiting embodiments of the present technology, a respective configuration of the aligner 20 may be applied to the upper teeth 13 of the subject for treating misalignment of at least some thereof—such as the given upper tooth 17. By so doing, the desired occlusion between the lower teeth 12 and the upper teeth 13 may be attained.

According to certain non-limiting embodiments of the present technology, the aligner 20 may be made of a polymer, such as a thermoplastic material. In other non-limiting embodiments of the present technology, the aligner 20 may be made of poly-vinyl chloride (PVC). In yet other non-limiting embodiments of the present technology, the aligner 20 may be made of polyethylene terephthalate glycol (PETG). Other suitable materials can also be used to form the aligner 20.

In some non-limiting embodiments of the present technology, the aligner 20 may be manufactured using additive manufacturing techniques, such as 3D printing techniques where the aligner 20 is formed by printing according to a pre-generated 3D representation thereof.

In other non-limiting embodiments of the present technology, the aligner 20 may be produced by a thermoforming process where (1) an unfinished aligner is produced, using a preform, on a respective aligner mold (not depicted) associated with a respective stage of the orthodontic treatment, which is configured to shape the inner surface 22 of the aligner 20; and (2) the unfinished aligner is cut along a predetermined cut line to remove excess material therefrom, thereby producing the aligner 20, the predetermined cut line defining the at least one edge of the channel 26 of the aligner 20, such as that of the front edge 28.

In specific non-limiting embodiments of the present technology, the aligner 20 may be manufactured in accordance with one or more methods described in a co-owned U.S. Pat. No. 11,191,618-B1, issued on Dec. 7, 2021, and entitled "SYSTEMS AND METHODS FOR FORMING A DENTAL APPLIANCE," the content of which is incorporated herein by reference in its entirety.

Also, in certain cases, as mentioned hereinabove, to attain the desired position between the lower and upper arch forms 10, 11, associated with the desired occlusion between the at least some of the lower and upper teeth 12, 13, the outer surface 24 of the aligner 20 can be modified. Conventionally, the outer surface 24 can define additional elements that are configured to interact when respective configurations of the aligner 20 are applied to each one of the lower and upper teeth 12, 13.

Figure 3:
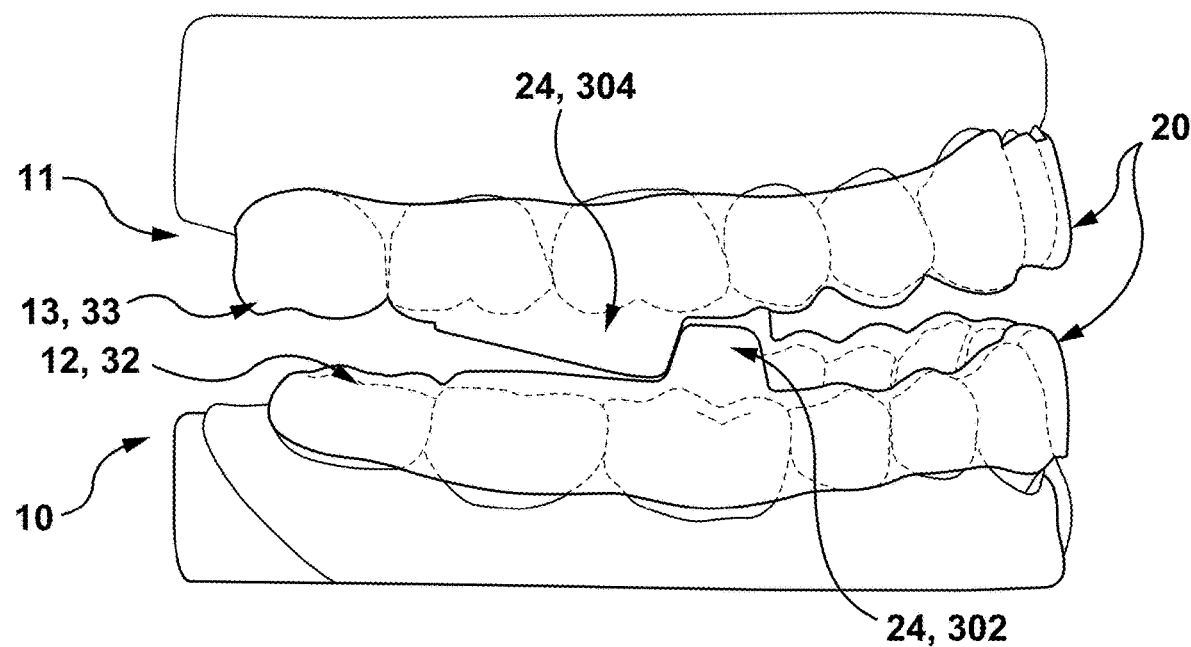
FIG. 3 depicts a schematic diagram of a prior art approach to causing the lower arch form to move to and remain in a desired position relative to the upper arch form, in accordance with certain non-limiting embodiments of the present technology.

With reference to FIG. 3, there is depicted an example prior art modification to the outer surface 24 of the aligner 20 for retaining the lower arch form 10 in the desired relative position to the upper arch form 11, in accordance with certain non-limiting embodiments of the present technology.

As it can be appreciated, in the example depicted in FIG. 3, the outer surface 24 of a first configuration of the aligner 20 applied to the lower teeth 12, along a lower occlusal surface 32 thereof, defines a first surface element 302. Further, the outer surface 24 of a second configuration of the aligner 20 applied to the upper teeth 13, along an upper occlusal surface 33 thereof, defines a second surface element 304, which is configured to engage (or interact) with the first surface element 302.

In the context of the present specification, the term "occlusal surface" of teeth, such as one of the lower and upper occlusal surfaces 32, 33 of the lower and upper teeth 12, 13, denotes a respective plurality of top surfaces of crowns of a given one of the lower and upper teeth 12, 13 that, at least partially, come in contact, or otherwise occlude, with an opposing one of the lower and upper teeth 12, 13 in a current bite position between the lower and upper arch form 10, 11, when a mouth of the subject is naturally closed. In such a position of the lower and upper arch forms 10, 11, the lower and upper occlusal surfaces 32, 33 of the lower and upper teeth 12, 13 form a current occlusion therebetween, such as one of the malocclusions mentioned above with reference to FIGS. 1A and 1B.

Thus, when such configurations of the aligner 20 are applied to the lower and upper teeth 12, 13 and when the subject closes their mouth, the first surface element 302 associated with the lower teeth 12 would engage with the second surface element 304 associated with the upper teeth 13 not letting the lower arch form 10 retract backwards to the state, for example, of the overbite thus causing the lower arch form 10 to move from the current to the desired position relative to the upper arch form 11.

The configurations of the first and second surface elements 302, 304 are not limited. In some non-limiting embodiments of the present technology, as depicted in FIG. 3, each one of the first and second surface elements 302, 304 can be implemented as protrusions configured to engage with each other. However, in other non-limiting embodiments of the present technology, a given one of the first and second surface elements 302, 304 can be a protrusion, and an other one of the first and second surface elements 302, 304 can be a respective indent configured to receive the protrusion, thereby interlocking the lower arch form 10 with the upper arch form 11 in the desired relative position therebetween.

Further, while the lower arch form 10 is retained in the desired position, the respective configuration of the aligner 20 can be configured to cause movements of the upper and/or lower teeth 12, 13 including, for example, tipping movements of at least one of the anterior ones of the upper and lower teeth 12, 13, as described above, to their respective target positions, in which the lower occlusal surface 32 and the upper occlusal surface 33 form the desired occlusion, such as the normal occlusion defined above with reference to FIG. 1C.

However, such additional elements defined in the outer surface 24 of the aligner 20, as being foreign objects to the subject's mouth, may cause additional discomfort of wearing the aligner 20 in the course of the orthodontic treatment. Also, such elements may produce additional pressure onto at least some of the lower and upper teeth 12, 13 causing pain to the subject.

Thus, the developers of the present technology have appreciated that the desired position of the lower arch form 10 with respect to the upper arch form 12 can be caused and further retained by a more subtle yet more anatomical modification of the outer surface 24 of the aligner 20, causing less discomfort to the subject. More specifically, the developers have devised methods and systems of producing the aligner 20 having a configuration of the outer surface 24 representative of a modified configuration of the given one of the lower and upper occlusal surfaces 32, 33, corresponding to a position of the respective one of the lower and upper teeth 12, 13 having been moved towards the desired occlusion.

Thus, the so modified configuration of the outer surface 24 of the aligner 20, when the latter is applied, for example, to the lower teeth 12, would simulate the desired occlusion with the upper teeth 13, causing the lower arch form 10 to remain in the desired position relative to the upper arch form 11. At the same time, the aligner 20 can be configured to apply, via the channel 26 defined by the inner surface 22, the forces to the respective one of the lower and upper teeth 12, 13 causing them to move towards their target positions corresponding to the desired occlusion between the lower and upper teeth 12, 13.

Thus, by using specifics of the intraoral anatomy of the subject, that is, the modified configuration of the given one of the lower and upper occlusal surfaces 32, 33, to bring the lower arch form 10 to the desired position relative to the upper arch form 11, a more comfortable configuration of the aligner 20 can be obtained, compared to the prior art approaches.

How the aligner 20 is produced having the so modified outer surface 24, according to certain non-limiting embodiments of the present technology, will be described in detail below with reference to FIGS. 11 to 17.

System

Figure 4:
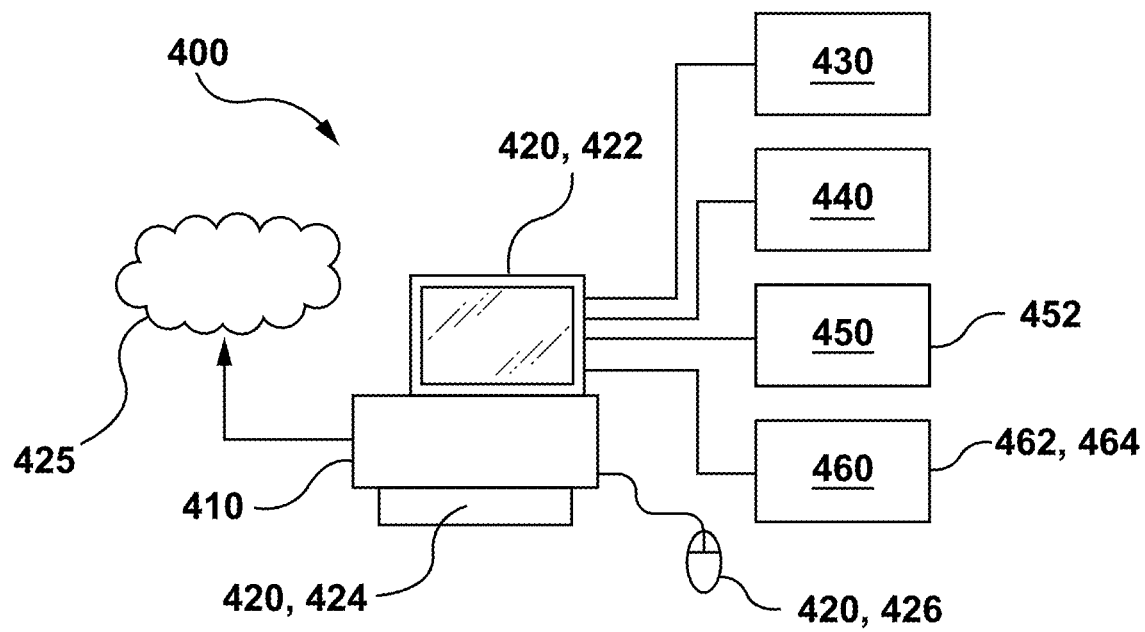
FIG. 4 depicts a schematic diagram of a computer system for making the orthodontic appliance of FIGS. 2A and 2B, in accordance with certain non-limiting embodiments of the present technology.
Figure 5:
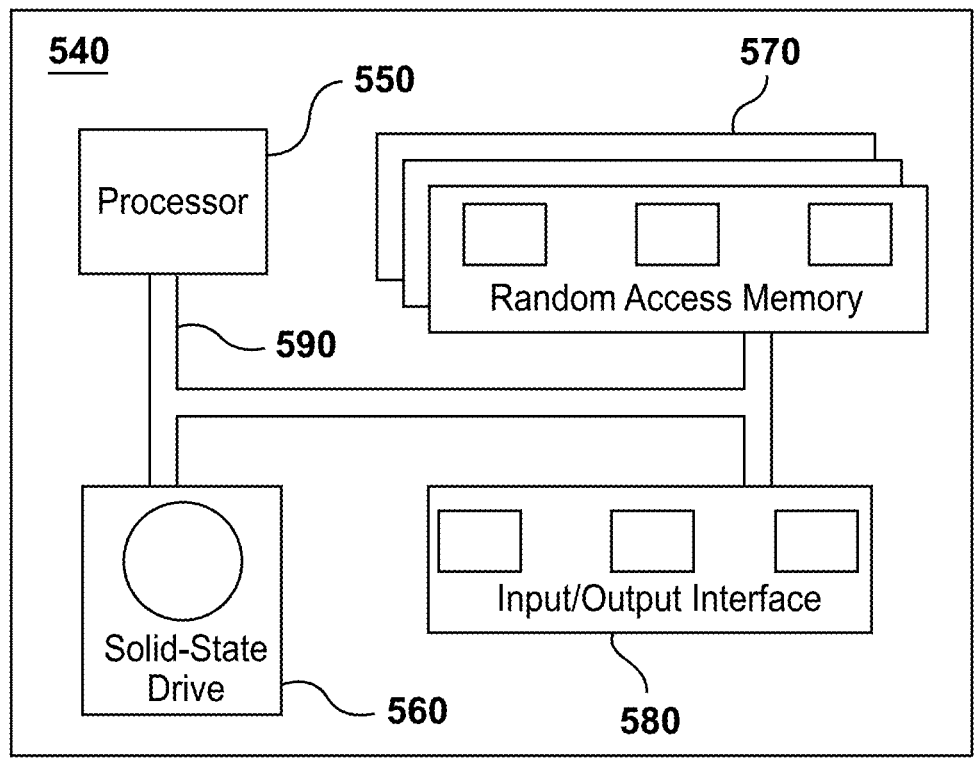
FIG. 5 depicts a schematic diagram of a computing environment, including a processor, of the system of FIG. 4, in accordance with certain embodiments of the present technology.

With reference to FIGS. 4 and 5, there is depicted a schematic diagram of a system 400 suitable for manufacturing the configuration of the aligner 20 mentioned above, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to determine, based on image data associated with the subject, such as the 3D digital model of a given one of the lower and upper arch forms 10, 11, a configuration of the aligner 20 configured for retaining the lower arch form in the desired position relative to the upper arch form 11. In additional non-limiting embodiments of the present technology, the computer system 410 may further be configured to produce at least one configuration of the aligner 20 for implementing the orthodontic treatment.

To that end, in some non-limiting embodiments of the present technology, the computer system 410 may be configured to receive image data pertaining to the subject or to a given stage of the orthodontic treatment. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a given tooth (not separately numbered) of the lower and upper teeth 12, 13, such as a crown portion thereof (also not separately numbered) extending outwardly of the gingival sulcus. In some embodiments, the image data is indicative of properties of internal portions of the anatomical structures, for example, volumetric properties of bone surrounding an internal portion of the given tooth of the lower and upper teeth 12, 13 extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

Further, as noted above, in some non-limiting embodiments of the present technology, the system 400 may be configured, based on a respective 3D digital model of the lower arch form 10, for example, determine the orthodontic treatment for the subject including forces to be applied onto the at least some of the lower teeth 12 to cause them to move to their respective target positions corresponding to the desired occlusion between the lower and the upper teeth 12, 13. In specific non-limiting embodiments of the present technology, the orthodontic treatment may be determined (for example, by a processor 550 depicted in FIG. 5) as described in a co-owned U.S. Pat. No. 10,993,782-B1 issued on May 4, 2021, and entitled "SYSTEMS AND METHODS FOR DETERMINING A TOOTH TRAJECTORY", a content of which is hereby incorporated by reference in its entirety.

In alternative non-limiting embodiments of the present technology, the computer system 410 may be configured to receive the image data associated with the subject directly from an imaging device 430 communicatively coupled thereto. Broadly speaking, the processor 550 may be configured to cause the imaging device 430 to capture and/or process the image data of the lower teeth 12 and the periodontium (not depicted) of the subject. In certain non-limiting embodiments of the present technology, the image data may include, for example, one or more of: (1) images of external surfaces of respective crown portions of the lower teeth 12, (2) images of an external surface of the periodontium including those of the lower gingiva 14, the alveolar mandibular bone (not depicted), and images of superficial blood vessels and nerve pathways associated with the lower teeth 12; and (3) images of an oral region. By doing so, the imaging device 430 may be configured, for example, to capture image data of the lower arch form 10 of the subject. In another example, the imaging device may also be configured to capture and/or process image data of an upper arch form (not depicted) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions of each one of the lower arch form 10 and upper arch form 11 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In yet other non-limiting embodiments of the present technology, the imaging device 430 can comprise a 3D laser scanner enabling to obtain a respective point cloud 3D digital model of each one of the lower arch form 10 and the upper arch form 11—such as by scanning a mold thereof and thus registering three-dimensional coordinates of points representative of the surface of the mold.

In a specific non-limiting example, the 3D laser scanner can be of one of the types available from LASER DESIGN LTD. of 5900 Golden Hills Drive, Minneapolis, MN 55416. It should be expressly understood that the desktop scanner can be implemented in any other suitable equipment.

Further, it is contemplated that the computer system 410 may be configured for processing of the received image data. The resulting image data of each one of the lower arch form 10 and then upper arch form 11 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

Further, in certain non-limiting embodiments of the present technology, the system 400 may be configured to produce at least one configuration of the aligner 20 based on the planned orthodontic treatment as mentioned above. To that end, the system 400 can further include a manufacturing system 440, to which the processor 550 can be configured to send respective instructions causing the manufacturing system 440 to produce the at least one configuration of the aligner 20. In some non-limiting embodiments of the present technology, the manufacturing system 440 can be a thermoforming system configured to produce an unfinished aligner (not depicted), for example, using a thermopriming process, in which a preform aligner (not depicted) is shaped on an aligner mold of the lower arch form 10—such as that produced according to an outer surface 3D digital model 1500, as will be described below.

In a specific non-limiting example, the thermoforming system can be of one of the types provided by HAMER LTD. of Rambla Antoni Gaudi, 108792 La Granada (Barcelona) Spain. It should be expressly understood that the thermoforming system can be implemented in any other suitable equipment.

Further, after the thermoforming the unfinished aligner, the system 400 can be configured to trim excess material thereof along a cut line to produce an edge of the aligner 20.

To that end, in some non-limiting embodiments of the present technology, the system 400 can be configured to determine (or otherwise receive) data indicative of the cut line and mark the cut line on the unfinished aligner. To that end, the system 400 may further comprise a marking subsystem 450. It is not limited how the marking subsystem 450 may be implemented; however, in various non-limiting embodiments of the present technology, the marking subsystem 450 may include a marking head 452 for applying the cut line onto the unfinished aligner and a first robotic arm (not depicted) for holding and manipulating the unfinished aligner (not depicted) around the marking head 452. In some non-limiting embodiments of the present technology, the marking head 452 may further comprise a coloring material storage (not depicted) for storing a coloring material (such as ink, as an example) and a supply control block (not depicted). In some non-limiting embodiments of the present technology, the marking head 452 may be implemented as a laser apparatus configurable to scorch the cut line (not depicted) on the unfinished aligner (not depicted).

In certain non-limiting embodiments of the present technology, the system 400 may further be configured to detect the cut line applied on the unfinished aligner and cut along the cut line to produce the aligner 20. In this regard, the system 400 may further comprise a forming subsystem 460. In some non-limiting embodiments of the present technology, the forming subsystem 460 may include a second robotic arm (not depicted), at an end-effector of which there is installed a camera device 462. In some non-limiting embodiments of the present technology, the camera device 462 can be any appropriate digital camera configured to detect the cut line applied by the marking subsystem 450 described above onto the unfinished aligner, including, for example, but not limited to, a coupled-charged device camera (a CCD camera). Further, as mentioned above, the forming subsystem 460 may include the cutting device 464. Non limiting examples of the cutting device 464 may include a laser-based cutting device, a mechanical cutting device such as using a blade with a rotary or linear cutting action, and a water-jet based cutting device, as an example.

In some non-limiting embodiments of the present technology, both the marking subsystem 450 and the forming subsystem 460 of the system 400 may be implemented as described in a co-owned U.S. patent application Ser. No. 16/704,718 filed on Dec. 5, 2019, entitled "SYSTEMS AND METHODS FOR FORMING PERSONALIZED DENTAL APPLIANCES", the content of which is hereby incorporated by reference in its entirety.

Thus, the forming subsystem 460 may be configured to: (1) cause the camera device 462 to move around the unfinished aligner (not depicted) with the cut line (not depicted) applied thereon to detect the cut line and generating respective image data thereof; (2) receive the image data of the cut line; and (3) based on the received image data of the cut line, cause cutting, by the cutting device 464 the unfinished aligner along the cut line, thereby forming the aligner 20.

In other non-limiting embodiments of the present technology, the forming subsystem 460 may be configured for cutting the unfinished aligner without requiring detection of the cut line. Instead, the determined cut line is used to guide the cutting—for example, based on received data indicative of a position of the cut line within the unfinished aligner. In some non-limiting embodiments of the present technology, the data indicative of the position of the cut line within the unfinished aligner may include at least one of: Cartesian coordinates; angular data indicative of a cutting angle for cutting the unfinished aligner; and a distance from the cutting device 464, as an example.

However, in other non-limiting embodiments of the present technology, the manufacturing system 440 can comprise an additive manufacturing system, such as a 3D printer, configured for direct manufacturing (printing) the at least one configuration of the aligner 20.

In a specific non-limiting example, the 3D printer can be of one of the types of HP Jet Fusion available from HP INC. of 1501 Page Mill Road, Palo Alto, CA, 94304, United States of America. It should be expressly understood that the 3D printer can be implemented in any other suitable equipment.

Further, with reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random-access memory 570 and an input/output interface 580. Communication between the various components of the computing environment 540 may be enabled by one or more internal and/or external buses 590 (e.g., a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller, and the like. Multiple examples of how the networking interface may be implemented will become apparent to the person skilled in the art of the present technology. For example, but without being limiting, the input/output interface 580 may implement specific physical layer and data link layer standard such as Ethernet™, Fibre Channel, Wi-Fi™ or Token Ring™. The specific physical layer and the data link layer may provide a base for a full network protocol stack, allowing communication among small groups of computers on the same local area network (LAN) and large-scale network communications through routable protocols, such as IP.

According to implementations of the present technology, the solid-state drive 560 stores program instructions suitable for being loaded into the random-access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (i.e., an "off the shelf" generic computer system). The generic computer system may be a desktop computer/personal computer but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer, or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera, or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Figure 6:
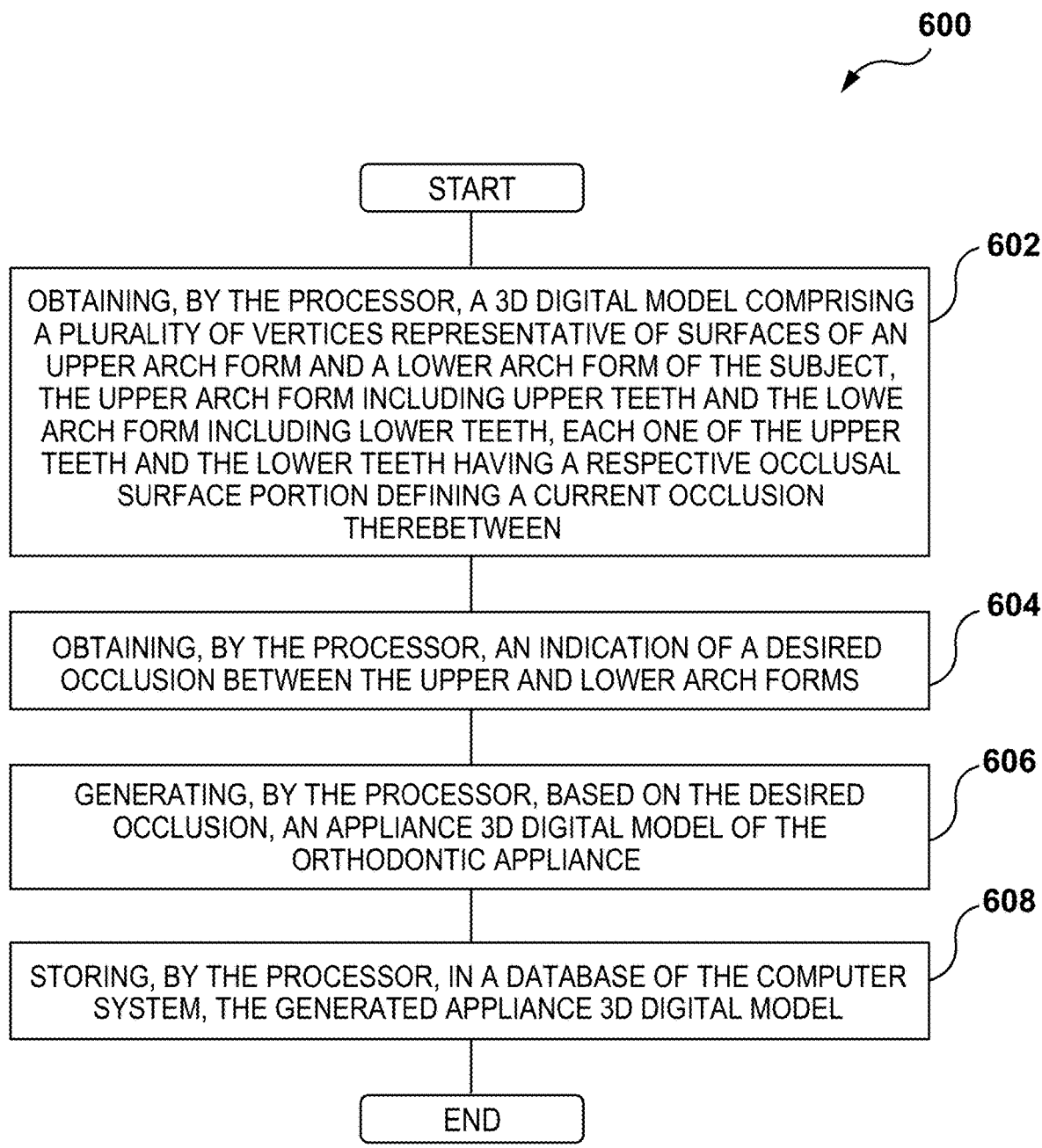
FIG. 6 depicts a flowchart diagram of a method for making the orthodontic appliance of FIGS. 2A and 2B, in accordance with certain non-limiting embodiments of the present technology.

Thus, given the architecture and examples provided above, it is now possible to execute a method of making an orthodontic appliance, such as the aligner 20 configured to displace the lower arch form 10 to the desired position, as described above. With reference to FIG. 6, there is depicted a schematic diagram of a method 600, in accordance with certain non-limiting of the present technology. For example, the method 600 can be executed by the processor 550 of the system 400.

Method

Step 602: Obtaining, by the Processor, a 3D Digital Model Comprising a Plurality of Vertices Representative of Surfaces of an Upper Arch Form and a Lower Arch Form of the Subject, the Upper Arch Form Including Upper Teeth and the Lower Arch Form Including Lower Teeth, Each One of the Upper Teeth and the Lower Teeth Having a Respective Occlusal Surface Portion Defining a Current Occlusion Therebetween The method 600 commences at step 602 with the processor 550 being configured to obtain the image data associated with the subject. More specifically, according to certain non-limiting embodiments of the present technology, the processor 550 can be configured to receive 3D digital models of at least one of the lower and upper arch forms 10, 11 of the subject.

Figure 7:
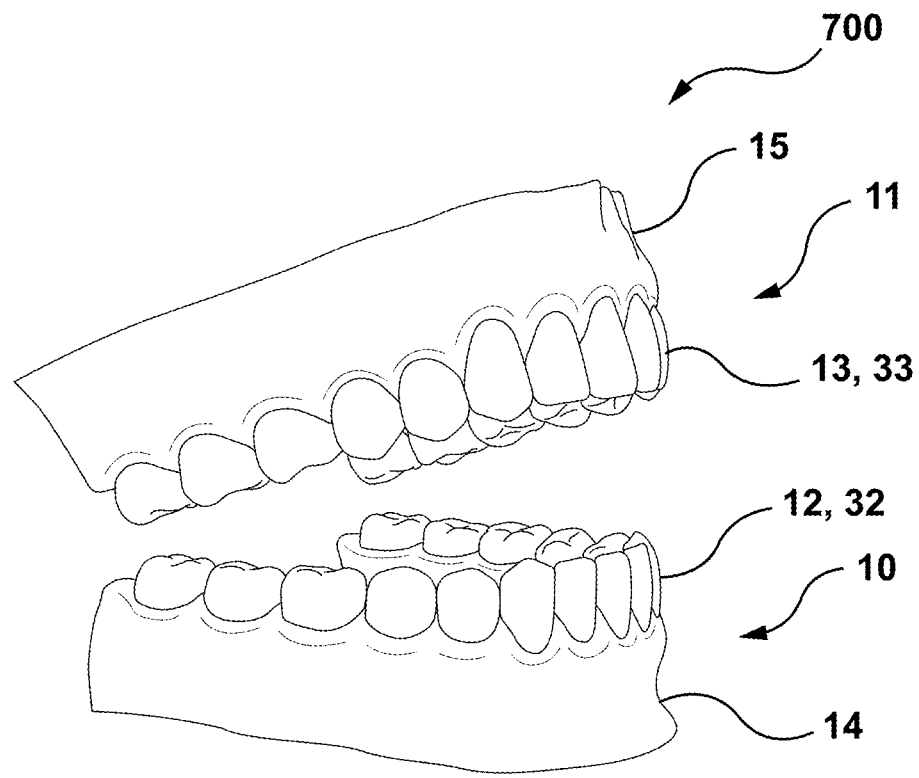
FIG. 7 depicts a 3D digital model of the lower and upper arch forms of the subject depicted in one of FIGS. 1A and 1B, in accordance with certain non-limiting embodiments of the present technology.

With reference to FIG. 7, there is schematically depicted a perspective view of a 3D digital model 700 representing the lower and the upper arch forms 10, 11, which can be used, by the processor 550 for determining a given configuration of the aligner 20, in accordance with certain non-limiting embodiments of the present technology. In some non-limiting embodiments of the present technology, the 3D digital model 700 can be representative of current configurations of the lower and the upper arch forms 10, 11. However, in other non-limiting embodiments of the present technology, the 3D digital model 700 can be representative of desired (or otherwise target) positions of at least some of the lower and upper teeth 12, 13 for a given stage of the orthodontic treatment, to which the at least some of the lower and upper teeth 12, 13 are to be caused to move by the channel 26 formed by the inner surface 22 of the aligner 20.

In some non-limiting embodiments of the present technology, the processor 550 can be configured to receive, from the imaging device 430 communicatively coupled with the processor 550, the 3D digital model 700 comprising a respective plurality of mesh elements (not depicted) representative of respective surfaces of the lower and upper arch forms 10, 11. For example, the imaging device 430 can be configured to generate the plurality of mesh elements including, without limitation, triangular mesh elements, quadrilateral mesh elements, convex polygonal mesh elements, or even concave polygonal mesh elements, as an example, without departing from the scope of the present technology.

However, in those embodiments where the imaging device 430 is the 3D laser scanner, the 3D digital model 700 comprises a 3D point cloud representative of the surfaces of the lower and upper arch forms 10, 11.

As noted above, according to the non-limiting embodiments of the present technology, the lower arch form 10 comprises the lower teeth 12 (also referred to herein as "mandibular teeth") and the lower gingiva 14; and the upper arch form 11 comprises the upper teeth 13 (also referred to herein as "maxillary teeth") and the upper gingiva 15. As it can be appreciated, each one of the lower and upper teeth 12, 13 are represented, in the 3D model 700, by respective crown and root portions thereof. However, in other non-limiting embodiments of the present technology, the lower and upper teeth 12, 13 can be represented only by their crown portions in the 3D digital model 700.

Also, in some non-limiting embodiments of the present technology, the processor 550 can be configured to obtain the 3D digital model 700 including independently generated 3D digital models of each one of the lower and upper arch forms 10, 11, not representing the current bite position of the subject. To that end, according to certain non-limiting embodiments of the present technology, the processor 550 can be configured to model, using the 3D digital model 700, the current bite position between the lower and upper arch forms 10, 11, which is indicative of a current occlusion between the lower and upper teeth 12, 13. It is not limited how the processor 550 can be configured to model, or otherwise reproduce, the current bite position between the lower and upper teeth 12, 13. For example, in some non-limiting embodiments of the present technology, the processor 550 can be configured to (i) obtain, for example, from the imaging device 430, another 3D digital model of the lower and upper arch form 10, 11 in the current bite position; (ii) register a current mutual position between certain predetermined reference points (not depicted) on the surfaces of the lower and upper arch forms in the current bite position; (iii) obtain the 3D digital model 700 including individual 3D digital models of each one of the lower and upper arch forms 10, 11; (iv) identify, on the surface of the lower and upper arch forms 10, 11 in the 3D digital model 700, the predetermined reference points; and (v) cause movement of at least one of the lower and upper arch forms 10, 11, within the 3D digital model 700, placing the predetermined reference points to the current mutual position.

However, in other non-limiting embodiments of the present technology, the processor 550 can be configured to model the current bite position between the lower and upper arch forms 10, 11 using one or more approaches described in a co-owned U.S. Pat. No. 11,364,103-B1, issued on Jun. 21, 2022, entitled "SYSTEMS AND METHODS FOR DETERMINING A BITE POSITION BETWEEN TEETH OF A SUBJECT", the content of which is incorporated herein by reference in its entirety.

More specifically, to determine the current bite position between the lower and upper arch form 10, 11, the processor 550 can be configured for: (i) determining, for each vertex of a first portion of the 3D model 700, representative of the lower arch form 10, a respective distance value therefrom to a second portion of the 3D model 700, representative of the upper arch form 11; (ii) determining, for each vertex of the first portion of the 3D model 700, a respective weight value, the respective weight value associated with a given vertex of the first portion of the 3D model 700 being indicative of a curvature of a surface of the 3D model thereat; (iii) generating, for each vertex of the first portion of 3D model 700 representative of the lower arch form 10, based on the respective weight value and the respective distance value associated therewith, a respective weighted distance value; aggregating respective weighted distance values associated with each vertex of the first portion thereby determining an aggregate distance value, the aggregate distance value being indicative of a remoteness measure of a current position of the first portion of the 3D model 700 from the current bite position thereof relative to the second portion of the 3D model 700; and minimizing the aggregate distance value to determine the current bite position of the lower arch form 10 and the upper arch form 11.

Figure 8:
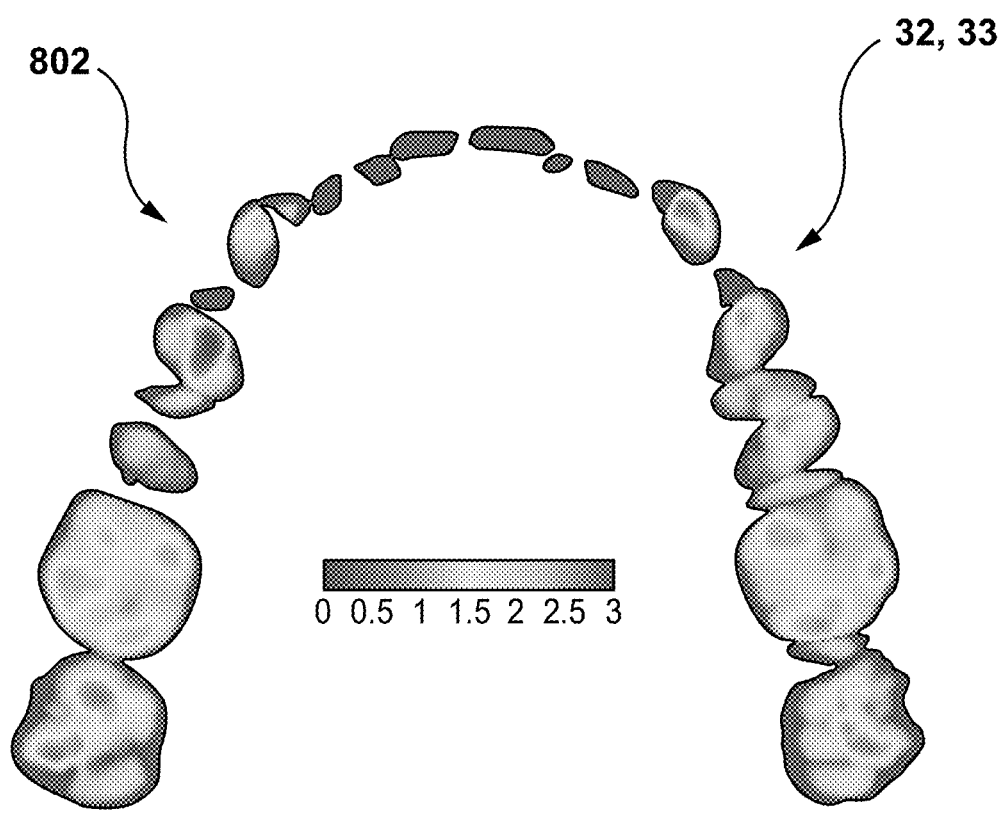
FIG. 8 depicts a schematic diagram of a depth map representing a topography of a current occlusion between the subject's teeth, in accordance with certain non-limiting embodiments of the present technology.

Further, in some non-limiting embodiments of the present technology, based on the so modelled current bite position, the processor 550 can be configured to cause visualisation of a topography of a current occlusion between the lower occlusal surface 32 and the upper occlusal surface 33, such as in the screen 422 of the system 400, for example, in a form of a current depth map representation 802 schematically depicted in FIG. 8, in accordance with certain non-limiting embodiments of the present technology.

As it can be appreciated, the current depth map representation 802 represents the respective distance values between the vertices of the 3D digital model 700 representative of the lower occlusal surface 32 and the upper occlusal surface 33 when the lower and upper teeth 12, 13 are positioned in the current bite position corresponding to the current occlusion therebetween. More specifically, in the current depth map representation 802, greater color intensity values are assigned to smaller values of the respective distance values between the lower and upper occlusal surfaces 32, 33, and vice versa.

The method 600 hence advances to step 604.

Step 604: Obtaining, by the Processor, an Indication of a Desired Occlusion Between the Upper and Lower Arch Forms At step 604, according to certain non-limiting embodiments of the present technology, the processor 550 can be configured to obtain an indication of the desired occlusion between the lower and upper arch forms 10, 11. In some non-limiting embodiments of the present technology, the processor 550 can be configured to obtain the indication of the desired occlusion between the lower and upper arch forms 10, 11, as wholes, that is, when only the at least some of the lower and upper teeth 12, 13, such as the first lower or upper molars, for example, form the desired occlusion. However, in other non-limiting embodiments of the present technology, the processor 550 can be configured to obtain the indication of the desired occlusion between each one of the lower teeth 12 and a respective one of the upper teeth 13.

In some non-limiting the processor 550 can be configured to obtain the indication of the desired occlusion from the practicing clinician who can modify the position of the lower teeth 12 relative to the upper teeth 13 within the 3D digital model 700 until the desired position therebetween is reached. Thus, depending on particular embodiments mentioned above, to provide the indication of the desired occlusion, the practicing clinician can: (i) modify the current position of the lower arch form 10 relative to the upper arch form 11, thereby modifying the position of the lower occlusal surface 32 relative to the upper occlusal surface 33, as a whole, such that the at least some of the lower teeth 12 form the desired occlusion with the upper teeth 13; or (ii) modify current positions of each one of the lower teeth 12 and/or each one of the upper teeth 13 individually, thereby redefining a respective one of the lower and upper occlusal surfaces 32, 33, such that each one of the lower teeth 12 forms the desired occlusion with the respective one of the upper teeth 13.

However, in other non-limiting embodiments of the present technology, the processor 550 can be configured to determine the desired occlusion automatically. For example, using the 3D digital model 700, the processor 550 can be configured to modify either one of the lower arch form 10 and each one of the lower teeth 12 individually, such that a relative position between the lower and upper occlusal surfaces 32, 33 satisfies at least one alignment condition. In some non-limiting embodiments of the present technology, the at least one alignment condition can include one of: overlapping occlusal surfaces of the lower and upper first molars; maximizing contact regions between the lower and upper occlusal surfaces 32, 33; an even distribution of the contact regions between the lower and upper occlusal surfaces 32, 33; and the like. Other alignment conditions for determining the desired occlusion between at least one of the lower teeth and upper teeth 12, 13 are also envisioned.

Figure 9:
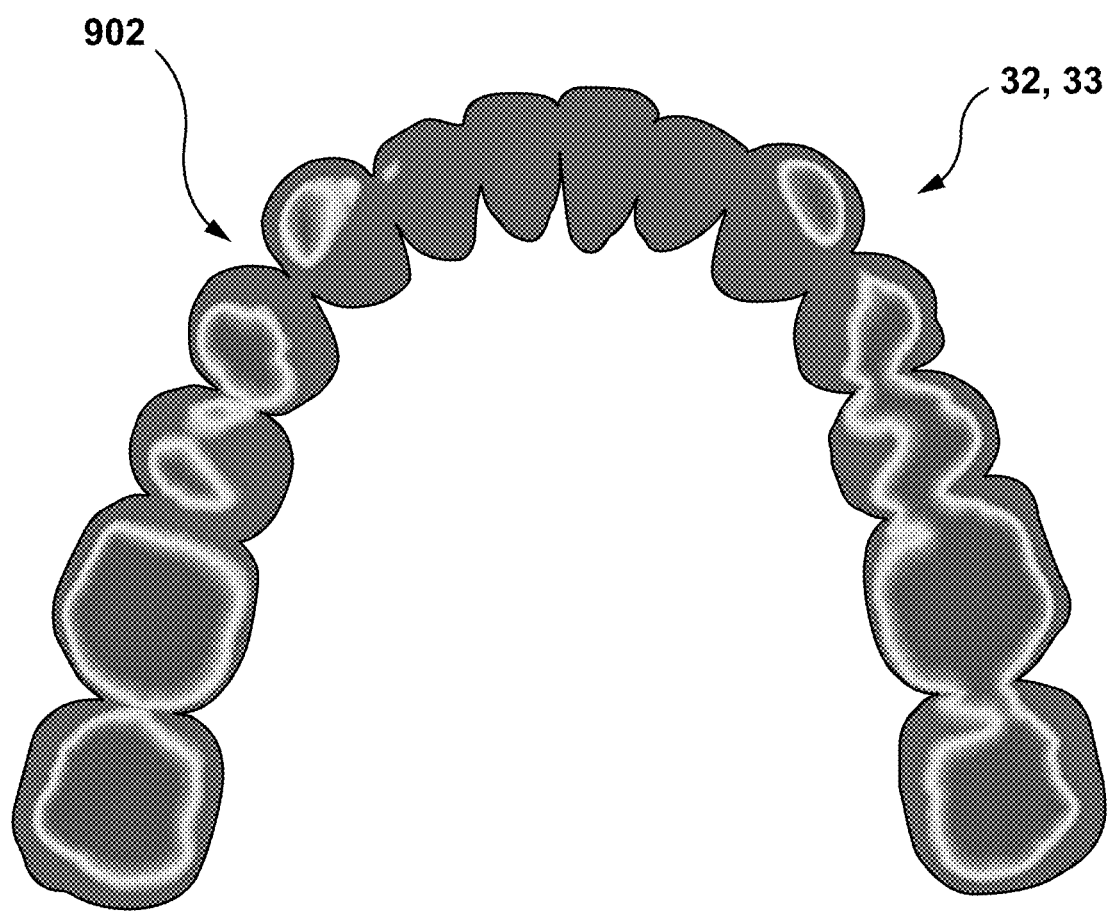
FIG. 9 depicts a schematic diagram of a depth map representing a topography of a desired occlusion between the subject's teeth, in accordance with certain non-limiting embodiments of the present technology.

Further, in some non-limiting embodiments of the present technology, the processor 550 can be configured to render a desired depth map representation 902 indicative of the so determined desired occlusion between the lower and upper teeth 12, 13, which is schematically depicted in FIG. 9, in accordance with certain non-limiting embodiments of the present technology.

The method 600 hence advances to step 606.

Step 606: Generating, by the Processor, Based on the Desired Occlusion, an Appliance 3D Digital Model of the Orthodontic Appliance At step 606, according to certain non-limiting embodiments of the present technology, based on the indication of the desired occlusion between the lower and upper teeth 12, 13 obtained at step 604, the processor 550 can be configured to generate a 3D digital model (such an aligner 3D digital model 1600 schematically depicted in FIG. 16) of the aligner 20 configured, when worn onto the subject's teeth, to retain the lower arch form 10 relative to the upper arch form 11 in the desired position, that is, that corresponding to the desired occlusion between the lower and upper teeth 12, 13.

More specifically, according to certain non-limiting embodiments of the present technology, the processor 550 can be configured to determine the aligner 3D digital model 1600 of the respective configuration of the aligner 20 to be applied to the teeth of the respective arch form, such as the lower teeth 12, whose outer surface would be representative of a configuration of the lower occlusal surface 32 corresponding to the desired occlusion between the lower and the upper teeth 12, 13, as illustrated by the desired depth map representation 902, which defines the outer surface 24 of the aligner 20. At the same, an inner surface of the aligner 3D digital model 1600, defining the inner surface 22 of the aligner 20, can be determined such that the inner surface 22 would be configured to receive at least some of the lower teeth 12 and exert the respective forces thereon causing them to move to their respective target positions.

Figure 12:
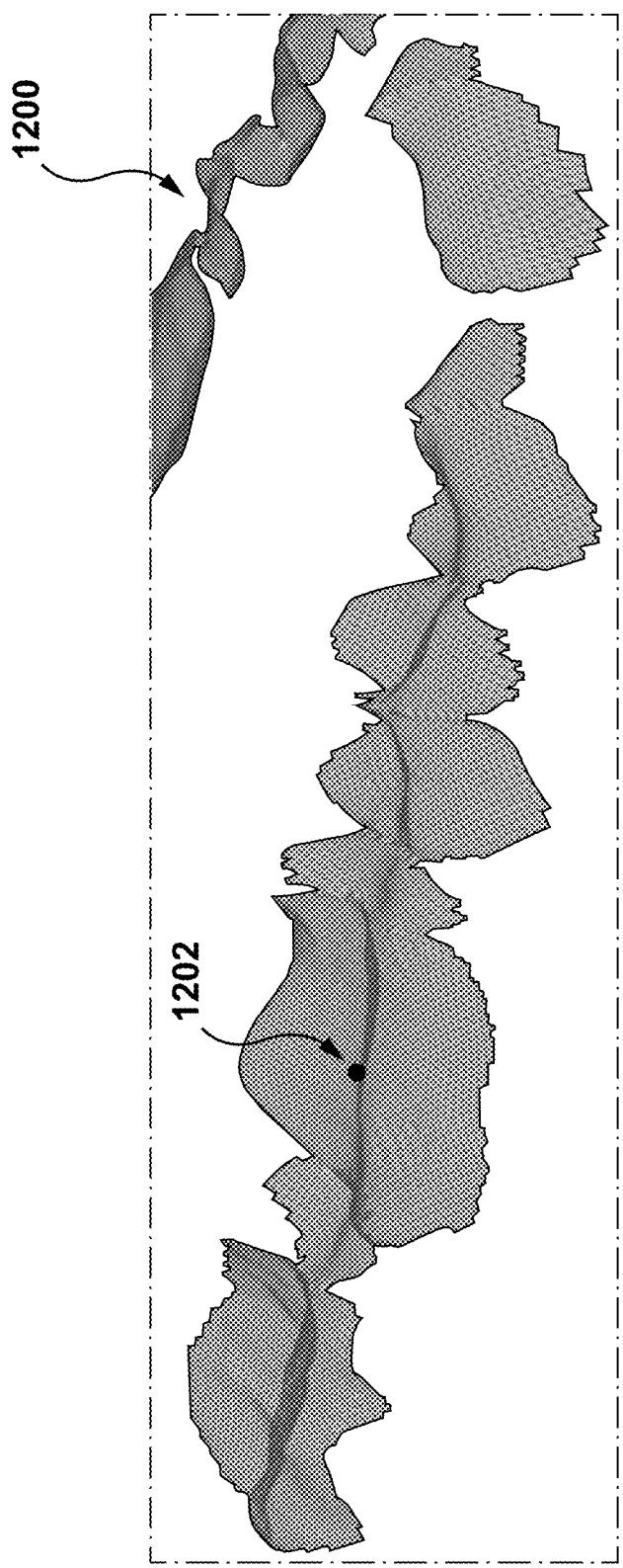
FIG. 12 depicts a schematic diagram of the occlusal surface 3D digital model, in accordance with certain non-limiting embodiments of the present technology.

To determine the outer surface of the aligner 3D digital model 1600, in accordance with certain non-limiting embodiments of the present technology, first, the processor 550 can be configured to determine a 3D digital model (such as an occlusal surface 3D digital model 1200 depicted in FIG. 12) representative of the contact regions between the lower and upper occlusal surfaces 32, 33 in the current bite position. In other words, the occlusal surface 3D digital model 1200 can be said to be representative of a topography of the current occlusion between the lower and upper teeth 12, 13. Further, as will be described in detail below, the processor 550 can be configured to (i) apply the occlusal surface 3D digital model 1200 to the 3D digital model 700 with a certain shift towards the desired occlusion between the lower and upper teeth 12, 13; and (ii) using the 3D digital model 700 with the occlusal surface 3D digital model 1200 applied thereon for determining the aligner 3D digital model 1600.

However, in other non-limiting embodiments of the present technology, as will be described in detail further below, the processor 550 can be configured to modify the outer surface directly on the aligner 3D digital model 1600. To that end, the processor 550 can be configured to (i) obtain a raw 3D digital model (such as a raw aligner 3D digital model 1700 depicted in FIG. 17) of the aligner 20, whose both the inner and outer surfaces have been determined based on the lower and upper occlusal surfaces 32, 33 in the current bite position; (ii) apply the occlusal surface 3D digital model 1200 to the raw aligner 3D digital model 1700 with the certain shift towards the desired occlusion between the lower and upper teeth 12, 13, thereby determining the aligner 3D digital model 1600.

Further, the processor 550 can be configured to cause manufacture of the given configuration of the aligner 20, as will be described yet further below.

Determining Occlusal Surface 3D Digital Model

According to certain non-limiting embodiments of the present technology, to determine the occlusal surface 3D digital model 1200, the processor 550 can be configured to (i) identify, in the 3D digital model 700, on the lower and upper occlusal surfaces 32, 33, pairs of vertices indicative of the current occlusion between; and (ii) based on the pairs of vertices, generate the occlusal surface 3D digital model 1200.

Figure 10:
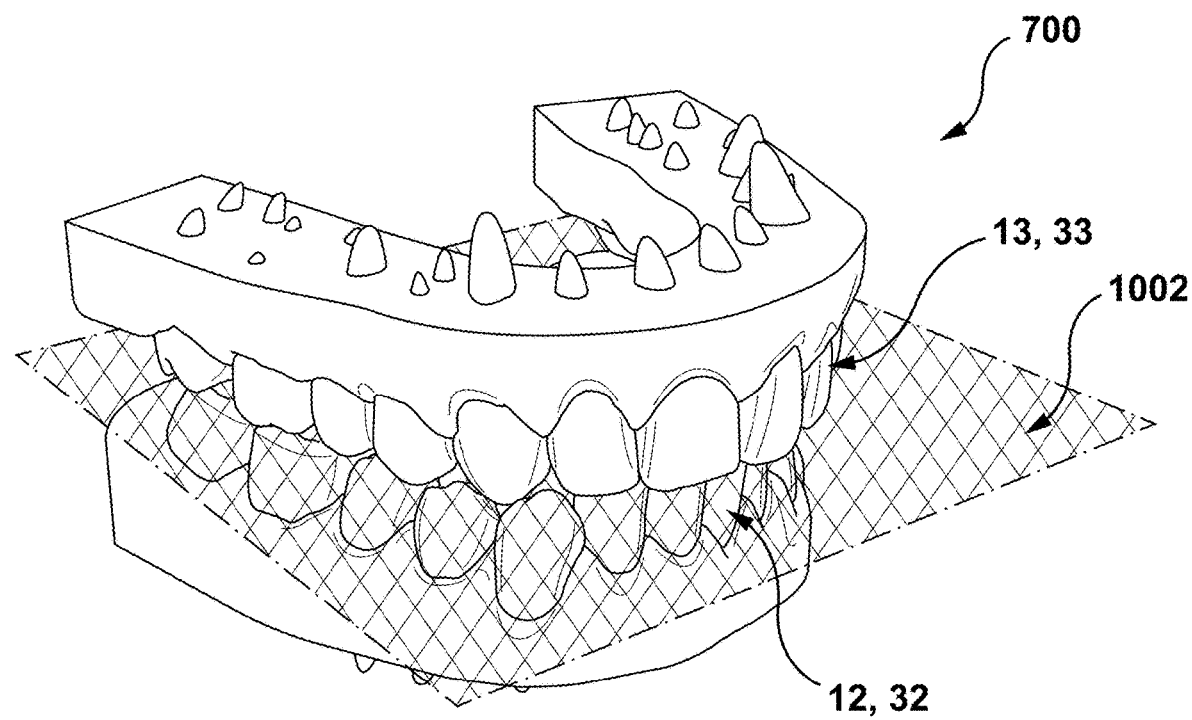
FIG. 10 depicts the 3D digital model of FIG. 7 with a representation of an occlusal plane extending between lower and upper subject's teeth, in accordance with certain non-limiting embodiments of the present technology.

According to certain non-limiting embodiments of the present technology, the processor 550 can be configured to determine vertices representative of the current occlusion based on an indication of an occlusal plane between the lower and upper teeth 12, 13. With reference to FIG. 10, there is depicted a schematic diagram of the 3D digital model 700 including a occlusal plane 3D digital model 1002 of the occlusal plane between the lower and upper occlusal surfaces 32, 33 in the current bite position, in accordance with certain non-limiting embodiments of the present technology.

In some non-limiting embodiments of the present technology, the processor 550 can be configured to determine the occlusal plane 3D digital model 1002 as extending between the lower and upper teeth 12, 13, touching incisal edges of anterior teeth (incisors) and cusps of posterior teeth thereof. In other non-limiting embodiments of the present technology, the processor 550 can be configured to determine the occlusal plane 3D digital model 1002 as a plane representing a mean curvature of at least one of the lower and upper occlusal surfaces 32, 33 of the lower and upper teeth 12, 13, respectively. However, in yet other non-limiting embodiments of the present technology, the occlusal plane 3D digital model 1002 may be predetermined by a practicing clinician, using, a specific articulator, such as a Fox Occlusal Plane Analyzer, as an example. It should be expressly understood that other techniques to determining the occlusal plane 3D digital model 1002 may also be used without departing from the scope of the present technology.

As it can be appreciated, akin to the 3D digital model 700, occlusal plane 3D digital model 1002 can comprise a plurality of mesh elements. In some non-limiting embodiments of the present technology, the processor 550 can be configured to generate the occlusal plane 3D digital model 1002 such that an edge length of a given one of the plurality of mesh elements is equal to that of a given one of the plurality of mesh elements defining the 3D digital model 700. Additionally, in some non-limiting embodiments of the present technology, after determining the position of occlusal plane 3D digital model 1002 between the lower and upper occlusal surfaces 32, 33, the processor 550 can be configured to re-distribute vertices defining the plurality of mesh elements of the occlusal plane 3D digital model 1002 uniformly.

Further, in some non-limiting embodiments of the present technology, to identify, in the 3D digital model 700, the pairs of vertices on the lower and upper occlusal surfaces 32, 33 indicative of the current occlusion between the lower and upper teeth 12, 13, the processor 550 can be configured to project the vertices of the occlusal plane 3D digital model 1002 onto the lower and upper occlusal surfaces 32, 33.

Figure 11:
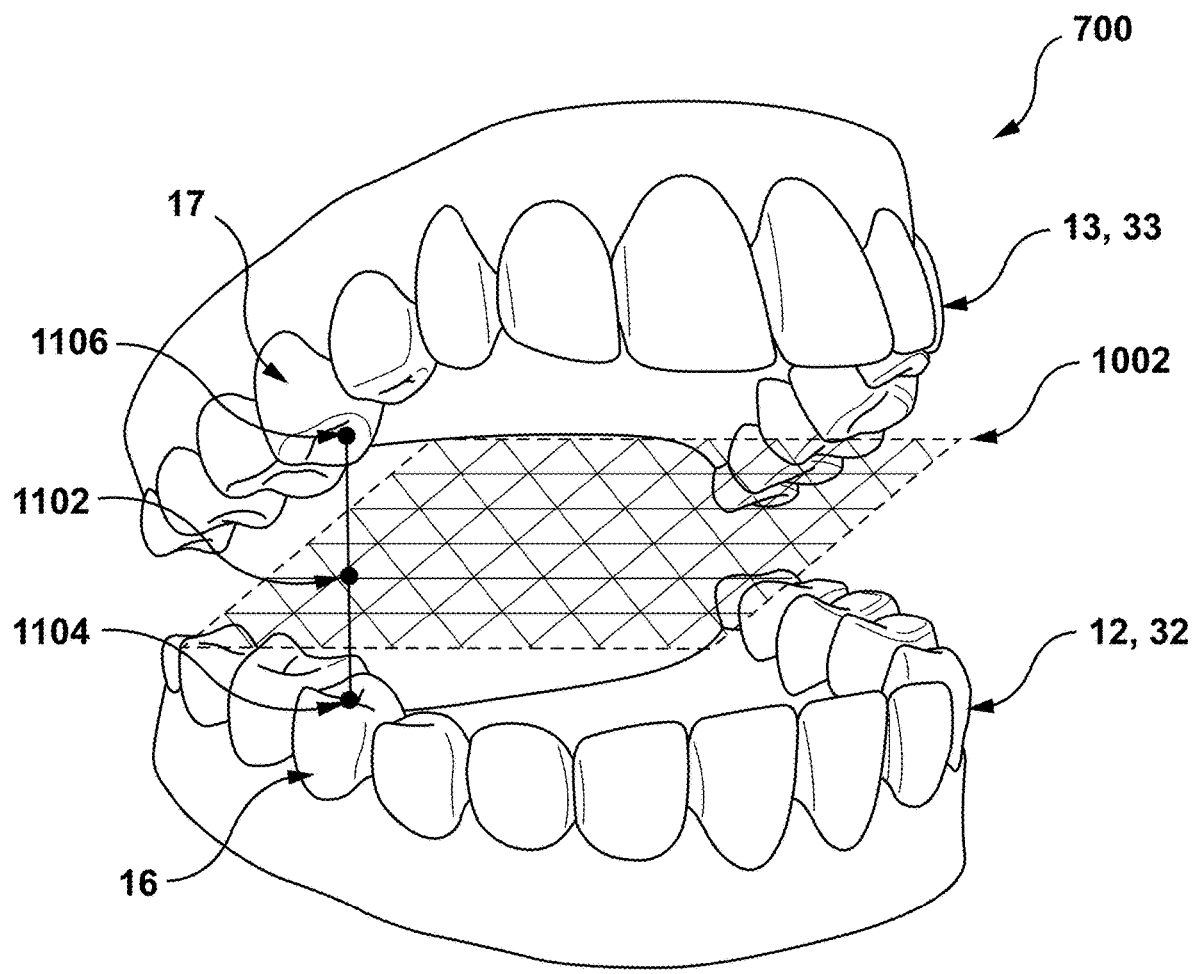
FIG. 11 depicts a schematic diagram for translating, by the processor of FIG. 5, vertices of the 3D digital model of FIG. 7 to the representation of the occlusal plane to determine an occlusal surface 3D digital model, in accordance with certain non-limiting embodiments of the present technology.

With reference to FIG. 11, there is depicted a schematic diagram of a step for translating vertices defining the occlusal plane 3D digital model 1002 to each one of the lower and upper occlusal surfaces 32, 33 in the 3D digital model 700, in accordance with certain non-limiting embodiments of the present technology.

More specifically, according to certain non-limiting embodiments of the present technology, the processor 550 can be configured, based on a given occlusal plane vertex 1102 of the occlusal plane 3D digital model 1002, determine, along a predetermined vertical direction, (i) a lower translated vertex 1104 on the lower occlusal surface 32; and (ii) an upper translated vertex 1106 on the upper occlusal surface 33. It is not limited how the processor 550 can be configured to define the predetermined vertical direction for determining the lower and upper translated vertices 1104, 1106. In some non-limiting embodiments of the present technology, the predetermined vertical direction can be defined as being along a normal vector (not separately depicted) of the occlusal plane 3D digital model 1002. In other non-limiting embodiments of the present technology, the predetermined vertical direction can be defined as being along one of a rotational and translational movement of the lower arch form 10 relative to the upper arch form 11, as an example.

In additional non-limiting embodiments of the present technology, the predetermined vertical direction for translating the given occlusal plane vertex 1102 to each one of the lower and upper occlusal surfaces 32, 33 can be defined to be along a tooth axis of a given tooth, to whose occlusal surface the given occlusal plane vertex 1102 is being translated. More specifically, the processor 550 can be configured to translate the given occlusal plane vertex 1102, within the 3D digital model 700, to the lower occlusal plane 32 along a respective tooth axis (not depicted) associated with a given lower tooth 16. Similarly, the processor 550 can be configured to translate the given occlusal plane vertex 1102, within the 3D digital model 700, to the upper occlusal plane 33 along the respective tooth axis (not depicted) associated with a given upper tooth 17.

It is not limited how the processor 550 can be configured to determine the respective tooth axis associated with the given tooth—such as that of one of the given lower and upper teeth 15, 16. In some non-limiting embodiments of the present technology, the processor 550 can be configured to determine the respective tooth axis in accordance with one of the approaches described in co-owned U.S. Pat. No. 10,856,954-B1 issued on Dec. 8, 2020 and entitled "SYSTEMS AND METHODS FOR DETERMINING TOOTH CENTER OF RESISTANCE", the content of which is incorporated herein by reference in its entirety.

More specifically, in order to determine the respective central tooth axis, the processor 550 can be configured to: (i) receive image data associated with a tooth crown of the subject—such as the 3D digital model 700 including crown portions of each one of the given lower and upper teeth 16, 17; (ii) identify an internal reference point in the image data, the internal reference point being based on a predetermined internal reference point instruction for locating the internal reference point in a given tooth crown (for example, that of the given lower tooth 16) including obtaining a mesial point on a mesial side of the tooth crown, and a distal point on a distal side of the given tooth crown, generating a mesiodistal line joining the mesial point and the distal point, and identifying the mesiodistal center as a midpoint on the mesiodistal line; (iii) determine a reference plane in the image data, the reference plane being perpendicular to the mesiodistal line and extending through the mesiodistal center; (iv) determine an intersection curve based on an intersection of the reference plane and a representation of the given lower tooth 16, the intersection curve following a shape of the surface of the given tooth crown of the given lower tooth 16 at the reference plane; and (v) determine the respective tooth axis of the given tooth crown of the given lower tooth 16 based on the intersection curve.

Thus, by translating, in the 3D digital model 700, each one of the plurality of vertices defining the occlusal plane 3D digital model 1002 to each one of lower and upper occlusal surfaces 32, 33, respectively, the processor 550 can be configured to determine a plurality of lower translated vertices and a plurality of upper translated vertices. Thus, a given one of the plurality of lower translated vertices and a given one of the plurality of upper translated vertices form a respective one of the pairs of vertices representative of the current occlusion between the lower and upper teeth 12, 13, which the processor 550 can further be configured to use to determine the occlusal surface 3D digital model 1200.

Additionally, in some non-limiting embodiments of the present technology, the processor 550 can be configured to filter the pairs of vertices representative of the current occlusion. For example, in some non-limiting embodiments of the present technology, the processor 550 can be configured to remove from further considerations those pairs of vertices having a respective distance therebetween, along the predetermined vertical direction defined as described above, greater than a predetermined distance threshold value. It is not limited how the predetermined distance threshold value for filtering the pairs of vertices can be selected; and in some non-limiting embodiments of the present technology, the predetermined distance threshold value can be determined based on a thickness of the resulting configuration of the aligner 20. For example, in those embodiments where a maximum thickness of the aligner 20 has been predetermined to be 0.75 mm, the predetermined distance threshold value can be 3.0 mm.

However, in other non-limiting embodiments of the present technology, the predetermined distance threshold value can be selected based on trade-off between accuracy of generating the occlusal surface 3D digital model 1200 and an amount of computational resources consumed by the processor 550 for executing this step, and can comprise 1.5 mm, 2.0 mm, 2.5 mm, 3.5 mm, 4.0 mm, 4.5 mm, and the like.

Further, according to certain non-limiting embodiments of the present technology, the processor 550 can be configured to apply a predetermined rule to the so identified pairs of vertices to generate the occlusal surface 3D digital model 1200. More specifically, in some non-limiting embodiments of the present technology, the processor 550 can be configured to determine a given vertex of the occlusal surface 3D digital model 1200 as being a vertex positioned at a predetermined level along a line extending between a respective one of the pairs of vertices—such as the lower and upper translated vertices 1104, 1106, while the lower and upper teeth 12,13 are in the current bite position. For example, in some non-limiting embodiments of the present technology, the predetermined level can be a midlevel between the respective one of the pairs of vertices. However, in other non-limiting embodiments of the present technology, a value of the predetermined level is not limited and can comprise 0.1, 0.2, 0.4—that is, towards the lower occlusal surface 32; or 0.7, 0.8, 0.95, for example—that is, towards the upper occlusal surface 33, along the line extending between the respective one of the pairs of vertices.

Thus, the processor 550 can be configured to generate the occlusal surface 3D digital model 1200 representative of the topography of the current occlusion between the lower and upper teeth 12, 13, as schematically depicted in FIG. 12, in accordance with certain non-limiting embodiments of the present technology.

Also, in some non-limiting embodiments of the present technology, the processor 550 can further be configured to smooth the occlusal surface 3D digital model 1200. In some non-limiting embodiments of the present technology, the smoothing can include smoothing using a Harmonic function. In other non-limiting embodiments of the present technology, the processor 550 can be configured to smooth the surface of the occlusal surface 3D digital model 1200 by averaging positions of vertices along the predetermined vertical direction within a neighborhood (not depicted) of a predetermined number of vertices. More specifically, in these embodiments, the processor 550 can be configured to: (i) identify, around a given vertex of the occlusal surface 3D digital model 1200, the neighborhood of vertices including the predetermined number of vertices; (ii) determine, for each vertex of the neighborhood, a respective position thereof along the predetermined vertical direction, such as a respective distance thereof along the predetermined vertical direction from one of the lower and upper occlusal surfaces 32, 33; (iii) determine an average position among respective positions associated with each vertex of the neighborhood, such as an average distance between respective distances along the predetermined vertical direction; and (iv) assign the average position, along the predetermined vertical direction, to each vertex of the neighborhood. The predetermined number of vertices for the neighborhood can be selected based on a trade-off between a level of detail and a level of smoothness of the smoothed occlusal surface 3D digital model, and, in some non-limiting embodiments of the present technology, can comprise, for example, from 5 to 7 vertices. However, other numbers of vertices defining the neighborhood around the given vertex of occlusal surface 3D digital model 1200, such as 3, 4, or 10, 15, and 20, for example, are also envisioned without departing from the scope of the present technology. By doing so, the processor 550 can be configured to flatten kinks along the surface of the occlusal surface 3D digital model 1200, hence smoothing it.

Also, in some non-limiting embodiments of the present technology, the processor 550 can be configured to register, in the occlusal surface 3D digital model 1200, occlusal reference landmarks of at least one of the lower and upper occlusal surfaces 32, 33 for further application of the occlusal surface 3D digital model 1200 to the 3D digital model 700, as will be described below. More specifically, with continued reference to FIG. 12, the processor 550 can be configured to register at least one occlusal reference landmark 1202 corresponding to one or both of a respective lower teeth landmark (not depicted), defined within the lower occlusal surface 32, and a respective upper teeth landmark (also not depicted), defined within the upper occlusal surface 33. For example, to register the at least one occlusal reference landmark 1202, the processor 550 can be configured to translate at least one of the respective lower and upper teeth landmarks, along the predetermined vertical direction, as described above. Additionally, the processor 550 can be configured to register respective reference distance values from the at least one occlusal reference landmark 1202 to each one of the respective lower and upper teeth landmarks.

It is not limited how the processor 550 can be configured to select each one of the respective lower and upper teeth landmarks for registering the at least one occlusal reference landmark 1202. In some non-limiting embodiments of the present technology, the processor 550 can be configured to determine a given one of the respective lower and upper teeth landmarks (both not depicted) as being representative of an anatomical feature of the respective one of the lower and upper occlusal surface 32, 33, including, without limitation, various grooves, cusps, pits, and ridges of the lower and upper teeth 12, 13. For example, the processor 550 can be configured to determine the respective lower teeth landmark as being indicative of a cusp of a given lower molar of the lower teeth 12, further the processor 550 can be configured to determine, along the upper occlusal surface 33, the respective upper teeth landmark as a point being in contact (or closest, as an example) with the respective lower teeth landmark.

Further, the processor 550 can be configured to use the occlusal surface 3D digital model 1200 for generating the aligner 3D digital model 1600. To do so, the processor 550 can be configured to apply different approaches. In some non-limiting embodiments of the present technology, the processor 550 can be configured to apply the occlusal surface 3D digital model 1200 to at least one of the lower and upper teeth 12, 13 to generate a 3D digital model of the outer surface 24 of the aligner 20. However, in other non-limiting embodiments of the present technology, as mentioned above, the processor 550 can be configured to apply the occlusal surface 3D digital model 1200 to a raw 3D digital model of the aligner 20.

Determining an Outer Surface of the Aligner

According to certain non-limiting embodiments of the present technology, to determine the configuration of the outer surface 24 of the aligner 20, the processor 550 can be configured to: (i) position, using the at least one occlusal reference landmark 1202, the occlusal surface 3D digital model 1200 along the at least one of the lower and upper occlusal surfaces 32, 33, in the 3D digital model 700; (ii) move the occlusal surface 3D digital model 1200 towards the desired occlusion represented by desired depth map representation 902; and (iii) determine the 3D digital model of the outer surface 24 of the aligner 24 as being one of the lower and upper arch forms 10, 11 in the 3D digital model 700 with the occlusal surface 3D digital model 1200 applied thereon.

Figure 13:
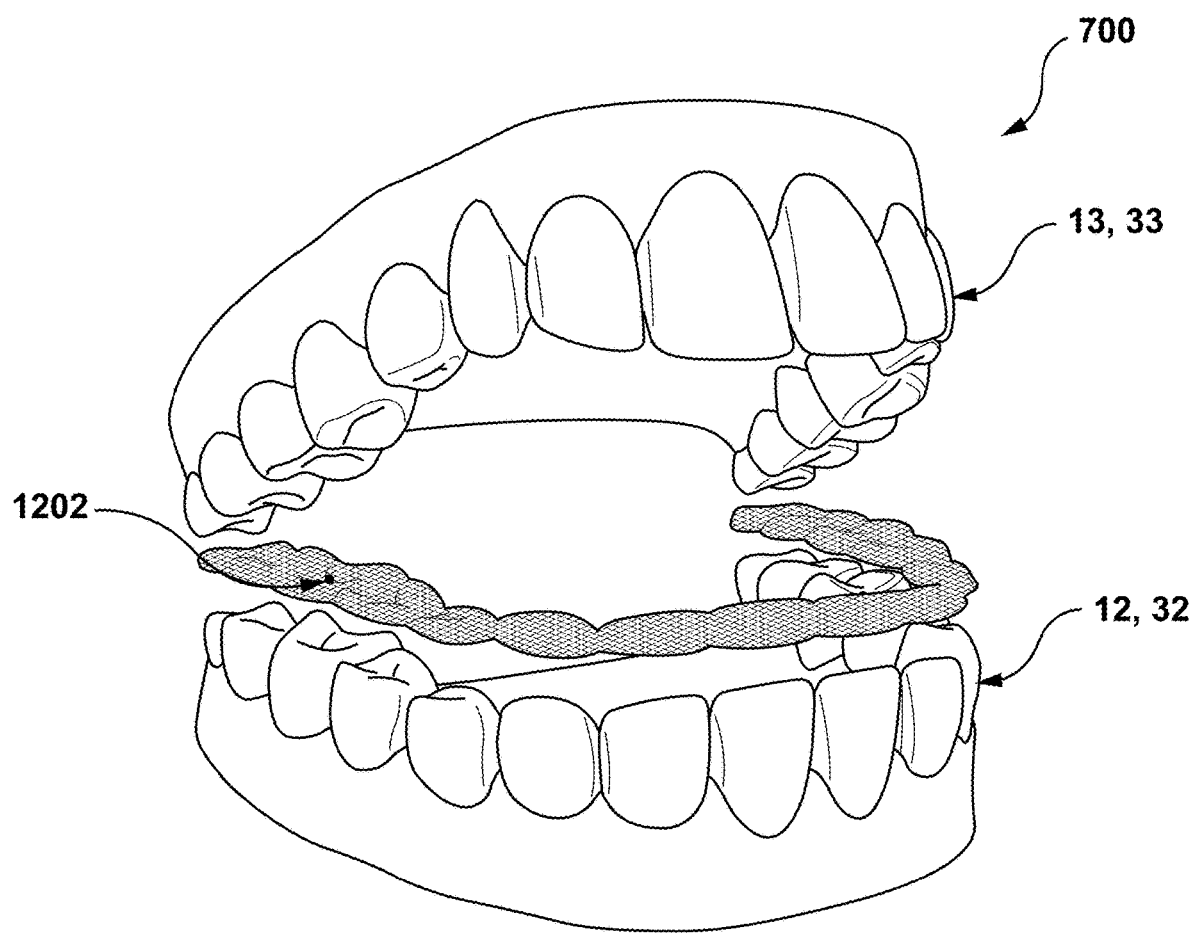
FIG. 13 depicts a schematic diagram of positioning, by the processor of FIG. 5, the occlusal surface 3D digital model of FIG. 12 over occlusal surfaces of subject's teeth in the 3D digital model of FIG. 7 with a shift, in accordance with certain non-limiting embodiments of the present technology.

With reference to FIG. 13, there is depicted a schematic diagram of the occlusal surface 3D digital model 1200 positioned between the lower and upper occlusal surfaces 32, 33 in the 3D digital model 700, in accordance with certain non-limiting embodiments of the present technology.

As mentioned hereinabove, the processor 550 can be configured to position the occlusal surface 3D digital model 1200 along at least one of the lower and upper occlusal surfaces 32, 33 in the 3D digital model 700 by aligning the at least one occlusal reference landmark 1202 with one or both of the respective lower teeth landmark and the respective upper teeth landmark (both not depicted), defined on the lower and upper occlusal surfaces 32, 33 as described above, such that current respective distance values between each one of the respective lower and upper teeth landmarks and the at least one occlusal reference landmark 1202 correspond to the respective reference distance values registered, as mentioned above.

Further, the processor 550 can be configured to move the occlusal surface 3D digital model 1200 towards the desired occlusion between the lower and upper teeth 12, 13, indication of which the processor 550 has received at step 604. To that end, the processor 550 can be configured to determine a shift between the current and desired occlusion, and further apply the determined shift to the occlusal surface 3D digital model 1200 in the 3D digital model 700.

More specifically, in those non-limiting embodiments of the present technology, where the processor 550 has received the indication of the desired occlusion between the lower and upper teeth 12, 13 by moving, in the 3D digital model 700, the lower arch form 10 relative to the upper arch form 11, as a whole, such that the at least some of the lower teeth 12 form the desired occlusion with the respective ones of the upper teeth 13, the processor 550 can be configured to determine the shift between the current and desired occlusions as a distance value therebetween. For example, in some non-limiting embodiments of the present technology, the processor 550 can be configured to determine the distance value along a shortest translational direction along the occlusal plane 3D digital model 1002 determined as described above, by comparing positions of the lower arch form 10 in the current and desired occlusions.

Further, in those embodiments, where the indication of the desired occlusion includes indication of the desired occlusion between each one of the lower teeth 12 and the respective one of the upper teeth 13, the processor 550 can be configured determine the shift as a shift vector. In some non-limiting embodiments of the present technology, a given value of the shift vector can include a respective distance value between positions of the given lower tooth 16 in the current and desired occlusions with the respective one of the upper teeth 13. Similarly, the processor 550 can be configured to determine the respective distance value along a shortest respective translational direction along the occlusal plane 3D digital model 1002.

Further, the processor 550 can be configured to apply the so determined shift to the occlusal surface 3D digital model 1200 along the at least one of the lower and upper occlusal surfaces 32, 33. In those embodiments where the shift is the distance value between the current and desired occlusions, as wholes, the processor 550 can be configured to shift the occlusal surface 3D digital model 1200 at the distance value along the at least one of the lower and upper occlusal surfaces 32, 33, towards the desired occlusion. For example, for correcting the overbite, in those embodiments where the respective configuration of the aligner 20 is to be applied to the lower teeth 12, the processor 550 can be configured to shift the occlusal surface 3D digital model 1200 at the distance value along the lower occlusal surface 32 anteriorly (forward). In another example, in those where the respective configuration of the aligner 20 is to be applied to the upper teeth 13 for correcting the overbite, the processor 550 can be configured to shift the occlusal surface 3D digital model 1200 at the distance value along the upper occlusal surface 33 posteriorly (backward). In yet other example, where the overbite is to be corrected by the configurations of the aligner 20 to be applied to both the lower and upper teeth 12, 13, the processor 550 can be configured to proportionally divide, such as 50/50, the distance value between two identical instances of the occlusal surface 3D digital model 1200 into a first distance value and a second distance value. Further, the processor 550 can be configured to apply: (i) the first distance value to a first instance of the occlusal surface 3D digital model 1200 along the lower occlusal surface 32 anteriorly; and (ii) the second distance value to a second instance of the occlusal surface 3D digital model 1200 along the upper occlusal surface 33 posteriorly.

In other non-limiting embodiments of the present technology, where the shift includes the shift vector, the processor 550 can be configured to shift each portion of the occlusal surface 3D digital model 1200, associated with a respective tooth of one of the lower and upper teeth 12, 13, to the respective distance value of the shift vector, along the respective one of the lower and upper occlusal surfaces 32, 33, towards the desired occlusion between the lower and upper teeth 12, 13. For example, to determine the respective configuration of the aligner 20 to be applied to the lower teeth 12, the processor 550 can be configured to shift the each portion of the occlusal surface 3D digital model 1200, associated with the respective tooth of one of the lower and upper teeth 12, along the lower occlusal surface 32.

Further, after applying the shift to the occlusal surface 3D digital model 1200 within the 3D digital model 700, the processor 550 can be configured to attach the occlusal digital model 1200 to the at least one of the lower and upper occlusal surfaces 32, 33 in the 3D digital model 700, thereby defining the outer surface 24 of a respective configuration of the aligner 20 to be applied to one or both of lower and upper teeth 12, 13.

Figure 14:
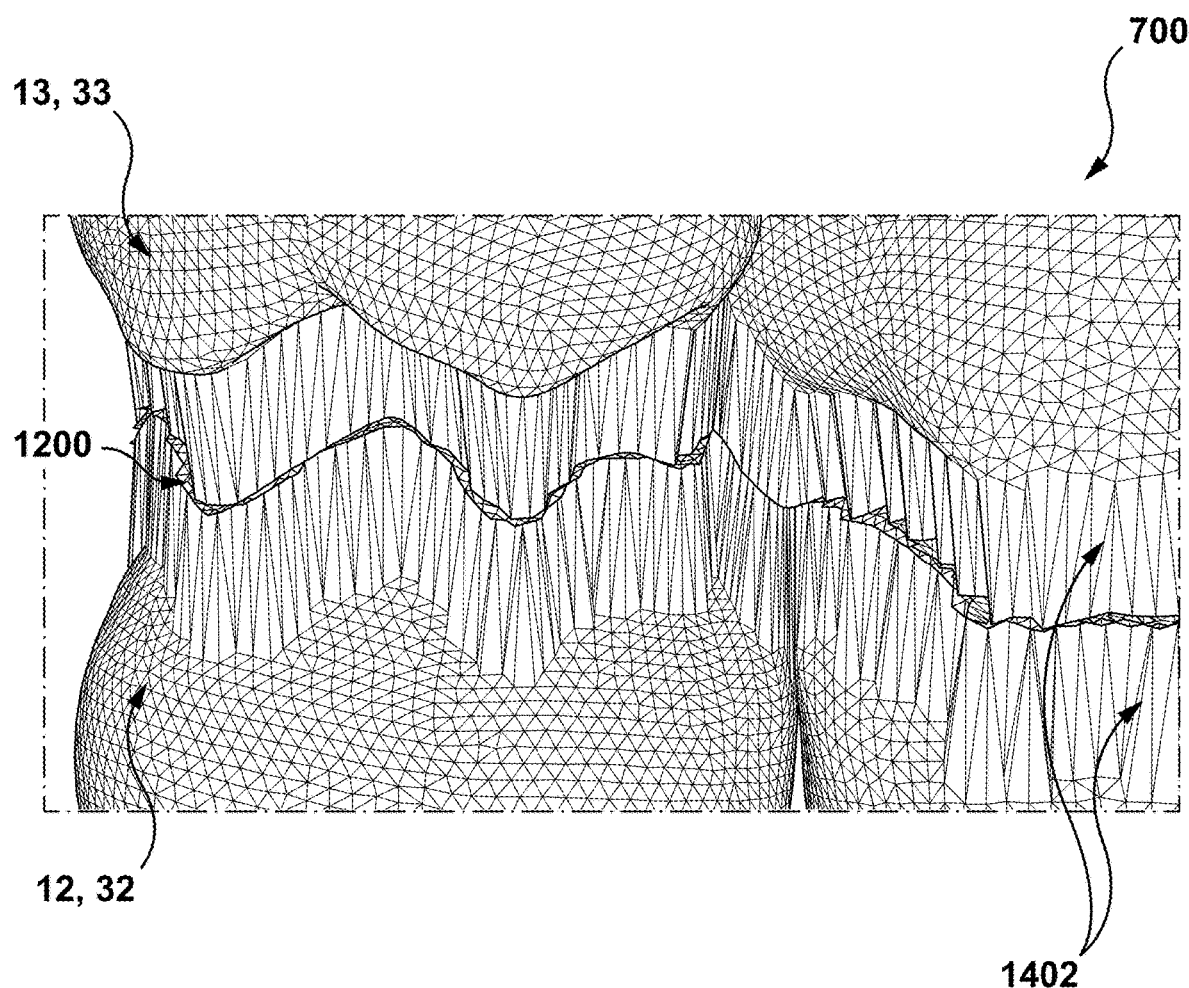
FIG. 14 depicts a schematic diagram of attaching, by the processor of FIG. 5, the occlusal surface 3D digital model of FIG. 12 to one of the occlusal surfaces of subject's teeth in the 3D digital model of FIG. 7 to the shift, in accordance with certain non-limiting embodiments of the present technology.

With reference to FIG. 14, there is depicted a schematic diagram of the occlusal surface 3D digital model 1200 attached to each one of the lower and upper occlusal surfaces 32, 33 in the 3D digital model 700, in accordance with certain non-limiting embodiments of the present technology.

As it can be appreciated from FIG. 14, the processor 550 can be configured to attach the occlusal surface 3D digital model 1200 to the a given one of the lower and upper occlusal surfaces 32, 33 in the 3D digital model 700 joining, by line segments, vertices defining the occlusal surface 3D digital model 1200 and those defining each one of the lower and upper occlusal surfaces 32, 33 in the 3D digital model 700, thereby defining side edges 1402.

Further, in some non-limiting embodiments of the present technology, for determining a smoother 3D digital model of the outer surface 24 of the aligner 20, the processor 550 can be configured to apply, to each one of the side edges 1402 a respective weight value, indicative of a length of each of the side edges 1402. More specifically, according to certain non-limiting embodiments of the present technology, the processor 550 can be configured to assign, to a given edge of the side edges 1402, the respective weight value being one of: (i) 0 (zero) if the given edge originates from a vertex defining the edge of the occlusal surface 3D digital model 1200; (ii) from 0 to 1 (zero to one) if the given edge originates from a vertex of the occlusal surface 3D digital model 1200 positioned from the edge thereof within a predetermined distance; and (iii) 1 (one) if the given edge originates from a vertex of the occlusal surface 3D digital model 1200 positioned beyond the predetermined distance from the edge of the occlusal surface 3D digital model 1200.

It is not limited how respective weight values are distributed between 0 and 1 for those of the side edges 1402 originating from the vertices of the occlusal surface 3D digital model 1200 positioned within the predetermined distance from the edge of the occlusal surface 3D digital model 1200; and can include, according to some non-limiting embodiments of the present technology, a distribution according to one of a linear, square root, or quadratic function of a distance value between the edge and the predetermined distance value.

Further, in some non-limiting embodiments of the present technology, the predetermined distance value can be selected based on a trade-off between the desired smoothness of the 3D digital model of the outer surface 24 of the aligner 20 and an accuracy of reproducing the desired occlusion between the lower and upper teeth 12, 13 by applying thereto the resulting configuration of the aligner 20. For example, in some non-limiting embodiments of the present technology, the predetermined distance value can be selected as being 1.5 mm. However, other predetermined distance values for smoothing the surface of the 3D digital model of the outer surface 24, such as 0.5 mm, 1.0 mm, or 2.0 mm, or even 3 mm, are also envisioned.

Figure 15:
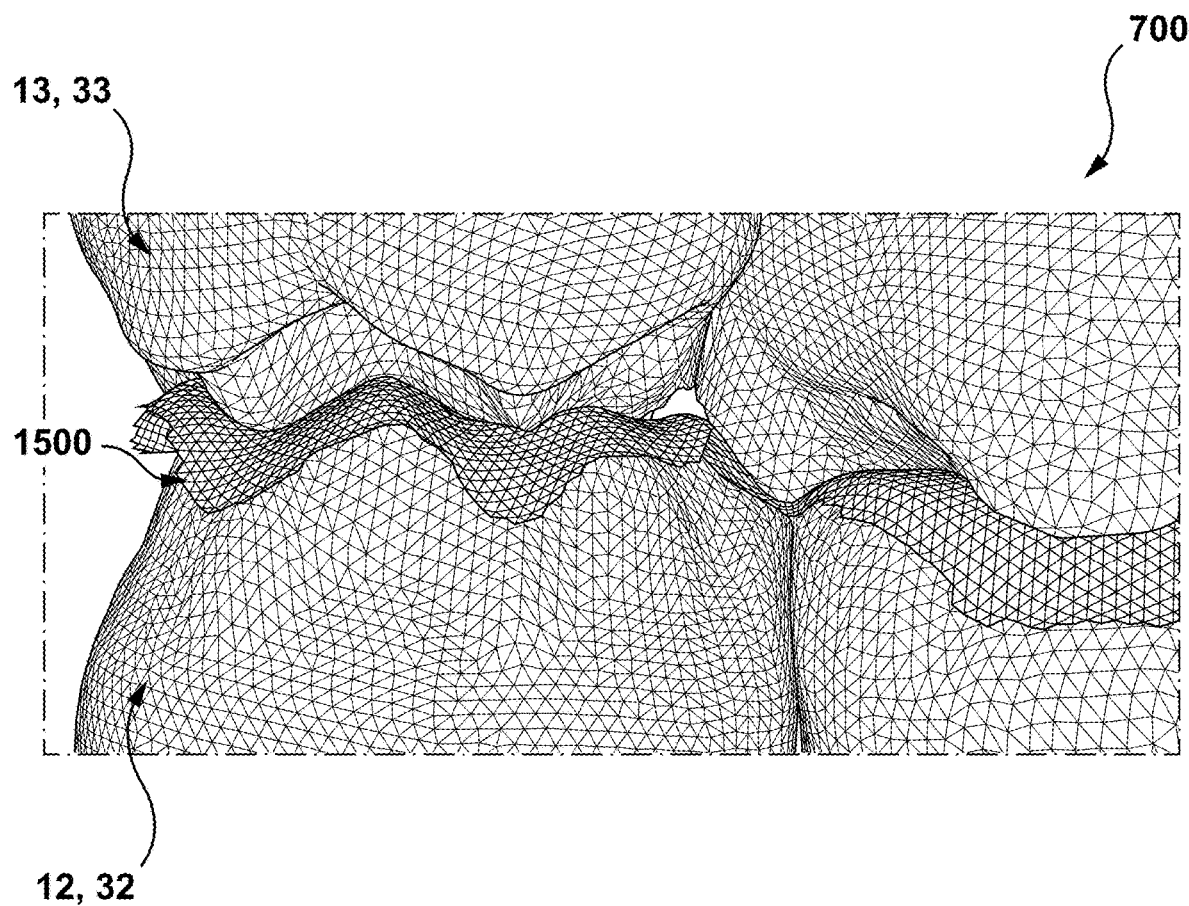
FIG. 15 depicts a schematic diagram of a 3D digital model of an outer surface of the orthodontic appliance of FIGS. 2A and 2B, generated by applying the occlusal surfaces of subject's teeth of FIG. 12 to the 3D digital model of FIG. 7 with the shift, in accordance with certain non-limiting embodiments of the present technology.

Thus, by attaching the occlusal surface 3D digital model 1200 to the one of the lower and upper occlusal surfaces 32, 33 in the 3D digital model 700, the processor 550 can be configured to generate the 3D digital model of the outer surface 24 of the aligner 20, such as an outer surface 3D digital model 1500, schematically depicted in FIG. 15, in accordance with certain non-limiting embodiments of the present technology.

As it can be appreciated, the outer surface 3D digital model 1500 is representative of the outer surface 24 of the configuration of the aligner 20 for the lower teeth 12. However, a similar approach to that described above can be applied, mutatis mutandis, to attach the occlusal surface 3D digital model 1200 to the upper occlusal surface 33 in the 3D digital model 700 to generate an other outer surface 3D digital model for the configuration of the aligner 20 to be applied to the upper teeth 13.

Further, based on the outer surface 3D digital model 1500, the processor 550 can be configured to determine the aligner 3D digital model 1600, as will be described below.

Determining an Aligner Configuration

Figure 16:
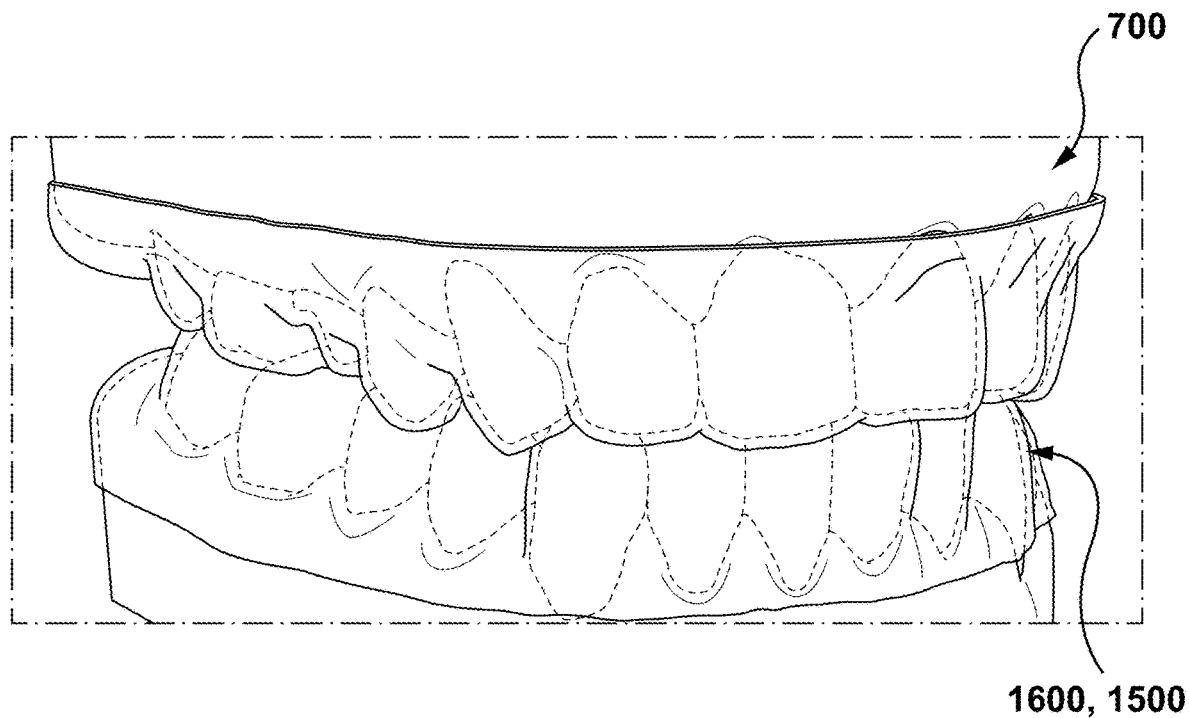
FIG. 16 depicts a respective view of an orthodontic appliance 3D digital model of the orthodontic appliance of FIGS. 2A and 2B, applied to the 3D digital model of FIG. 7, determined based on the 3D digital model of the outer surface depicted in FIG. 15, in accordance with certain non-limiting embodiments of the present technology.

With reference to FIG. 16, there is schematically depicted the aligner 3D digital model 1600 applied on the lower teeth 12 in the 3D digital model 700, in accordance with certain non-limiting embodiments of the present technology.

According to certain non-limiting embodiments of the present technology, based on the outer surface 3D digital model 1500, the processor 550 can be configured to determine the aligner 3D digital model 1600 such that the outer surface thereof closely follows the surface of the outer surface 3D digital model 1500, that is, a modified surface of the lower teeth 12 in the 3D digital model 700 after applying thereto the occlusal 3D digital model 1200 along the lower occlusal surface 32, defining the outer surface 24 of the aligner 20.

Further, in some non-limiting embodiments of the present technology, the inner surface of the aligner 3D digital model 1600 can have a configuration similar to that of the outer surface; and thus, in these embodiments, the inner surface 22 can correspond to the outer surface 24. However, in other non-limiting embodiments of the present technology, the inner surface of the aligner 3D digital model 1600 may have a different configuration from that of the outer surface. More specifically, in these embodiments, the inner surface of the aligner 3D digital model 1600 can closely follow the surfaces of the lower teeth 12 in the 3D digital model 700 prior to applying the occlusal 3D digital model 1200 along the lower occlusal surface 32, defining a configuration of the inner surface 22 of the aligner 20 that corresponds to the current occlusion between the lower and upper teeth 12, 13.

As it can be appreciated, the aligner 3D digital model 1600, when applied to the lower teeth 12, in the 3D digital model 700, causes the lower arch form 10 to remain in the desired position relative to the upper arch form 11, corresponding to the desired occlusion between the lower and upper teeth 12, 13.

Also, in some non-limiting embodiments of the present technology, the processor 550 can be configured to determine a single respective configuration of the aligner 20, by applying the shift to the occlusal surface 3D digital model 1200 in the 3D digital model 700, as described above, in its entirety, that is, all the shift at once.

However, in other non-limiting embodiments of the present technology, the processor 550 can be configured to distribute the shift among a plurality of configurations of the aligner 20 used for implementing the orthodontic treatment. More specifically, the processor 550 can be configured to determine, based on the shift, a plurality of shift intervals, each one of which is indicative of a respective portion of the distance value (or a respective portion of the given value of the shift vector) from the current to the desired occlusion. Further, the processor 550 can be configured to determine, based on the plurality of shift intervals, a respective plurality of outer surface 3D models of the outer surface 24, as described above, such that a given outer surface 3D digital model of the respective plurality of outer surface 3D digital models includes the occlusal 3D digital model 1200 shifted, along the at least one of the lower and upper occlusal surfaces 32, 33, by a respective one of the plurality of shift intervals, towards the desired occlusion.

In some non-limiting embodiments of the present technology, a number of shift intervals in the plurality of shift intervals can correspond to a number of configurations of the aligner 20 to be applied in the course of the orthodontic treatment. In other non-limiting embodiments of the present technology, the number of shift intervals can be less than the number of configurations of the aligner 20 applied during the orthodontic treatment, such that a given shift interval is applied to the occlusal surface 3D digital model for determining more than one configuration of the aligner 20. In some non-limiting embodiments of the present technology, a length of each shift interval of the plurality of shift intervals can be determined based on safety considerations, such as not to damage ligaments of one of temporomandibular joints of the subject. Also, in some non-limiting embodiments of the present technology, each one of the plurality of shift intervals can be equal.

Further, based on a given outer surface 3D digital model of the respective plurality of outer surface 3D models of the outer surface 24, the processor 550 can be configured to determine a respective aligner 3D digital model, based on which a respective one of the plurality of configurations of the aligner 20 can thus be produced, as will be described below.

Thus, the processor 550 can be configured to determine the aligner 3D digital model 1600 based on the outer surface 3D digital model 1500.

Figure 17:
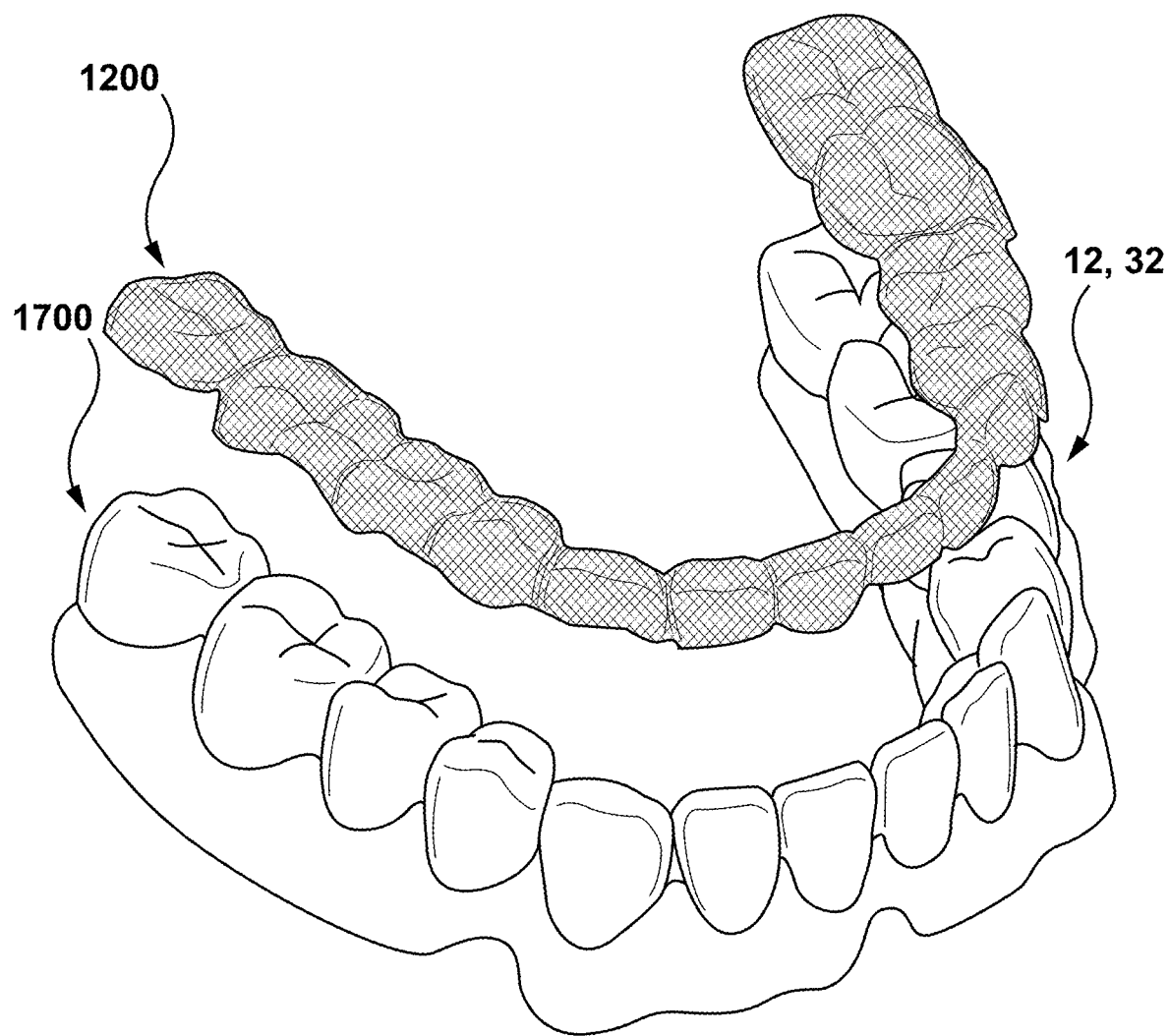
FIG. 17 depicts a schematic diagram of positioning, by the processor of FIG. 5, the occlusal surface 3D digital model of FIG. 12 over a raw orthodontic appliance 3D digital model of the orthodontic appliance of FIGS. 2A and 2B with the shift to determine the orthodontic appliance 3D digital model of FIG. 16, in accordance with certain non-limiting embodiments of the present technology.

However, in other non-limiting embodiments of the present technology, to determine the aligner 3D digital model 1600, the processor 550 can be configured to apply the occlusal 3D digital model 1200 directly to the raw aligner 3D digital model 1700. With reference to FIG. 17, there is depicted a schematic diagram of the raw aligner 3D digital model 1700 for the lower teeth 12, in accordance with certain non-limiting embodiments of the present technology.

More specifically, in these embodiments, the processor 550 can be configured to (i) obtain the raw aligner 3D digital model 1700, whose both outer and inner surfaces correspond to the current occlusion between the lower and the upper teeth 12, 13, as represented by the current depth representation 802 mentioned above; and (ii) apply, to the raw aligner 3D digital model 1700, the occlusal surface 3D digital model 1200 along the lower occlusal surface 32.

It is not limited how the processor 550 can be configured to obtain the raw aligner 3D digital model 1700. In some non-limiting embodiments of the present technology, the raw aligner 3D digital model 1700 can be generated by the imaging device 430 from a respective raw configuration of the aligner 20. In other non-limiting embodiments of the present technology, the processor 550 can be configured to determine the raw aligner 3D digital model 1700 based on the 3D digital model 700, without the occlusal 3D digital model 1200 applied thereon. Thus, similar to any one of the 3D digital models mentioned above, the raw aligner 3D digital model 1700 can include a plurality of mesh elements representative of a surfaces of the respective raw configuration of the aligner 20.

Further, the processor 550 can be configured to apply the occlusal surface 3D digital model 1200 to the raw aligner 3D digital model 1700, either with the whole shift or with a respective one of the plurality of shift intervals thereof, along the lower occlusal surface 32, as described above with respect to determining the outer surface 3D digital model 1500. By doing so, the processor 550 can be configured to determine a configuration of the outer surface 24, corresponding to the desired occlusion between the lower and upper teeth 12, 13, directly within the raw aligner 3D digital model 1700.

As it can be appreciated, the processor 550 can be configured to determine an other aligner 3D digital model for the configuration of the aligner 20 to be applied to the upper teeth 13 in a similar fashion, by applying, mutatis mutandis, the occlusal surface 3D digital model 1200 to an other raw aligner 3D digital having been generated for the upper teeth 13, as described above.

Thus, the processor 550 can be configured to determine the aligner 3D digital model 1600 by direct application of the occlusal surface 3D digital model 1200 to the raw aligner 3D digital model 1700.

The method 600 hence advances to step 608.

Step 608: Storing, by the Processor, in a Database of the Computer System, the Generated Appliance 3D Digital Model At step 608, according to certain non-limiting embodiments of the present technology, the processor 550 can be configured to store the data of the aligner 3D digital model 1600, such as in the solid-state drive 560 of the system 400, for further use in manufacturing the respective configuration of the aligner 20.

Further, in some non-limiting embodiments of the present technology, the processor 550 can be configured to cause the manufacturing system 440 to produce the respective configuration of the aligner 20 in accordance with the aligner 3D digital model 1600. More specifically, in those embodiments where the manufacturing system 440 is a thermoforming system, the aligner mold can be produced according to the outer surface 3D digital model 1500, that is, according to a portion of the 3D digital model 700 representative of the lower arch form 10 with the occlusal surface 3D digital model 1200 applied thereon with the shift towards the desired occlusion between the lower and upper teeth 12, 13, as described above. Further, the processor 550 can be configured to cause the manufacturing system 440 to produce the respective configuration of the aligner 20 according to the aligner molds, as described above with reference to FIG. 4.

However, in those embodiments where the manufacturing system 440 is an additive manufacturing system, the processor 550 can be configured to cause direct 3D-printing of the respective configuration of the aligner 20 according to the aligner 3D digital model 1600.

Embodiments where the processor 550 causes the manufacturing system 440 to produce the respective configuration of the aligner 20 without storing any one of the outer surface 3D digital model 1500 and the aligner 3D digital model 1600 are also envisioned without departing from the scope of the present technology.

The aligner 20 thus produced has the outer surfaces 24 corresponding to the desired occlusion between the lower and upper teeth 12, 13. More specifically, the outer surface 24 is representative of the modified surfaces of the lower teeth 12, as represented by the outer surface 3D digital model 1500, with the occlusal surface 3D digital model 1200 applied along the lower occlusal surface 32.

Thus, when the aligner 20 is applied to the lower teeth 12, it would cause the lower arch form 10, being in the current position, corresponding to one of the malocclusions depicted in FIGS. 1A and 1B, to move to the desired position relative to the upper arch form 11, the desired position corresponding to the desired occlusion between the at least some of the lower and upper teeth 12, 13, such as the normal occlusion as depicted in FIGS. 1C. At the same time, the inner surface 22 defines the channel 26 configured to receive the surfaces of the lower teeth 12, as represented by the 3D digital model 700, prior to the application of the occlusal surface 3D digital model 1200 and is thus configured to cause individual movements of the at least some of the lower teeth to their respective target positions, corresponding to the alignment within the lower arch form 10 and/or the desired occlusion, as an example.

The method 600 hence terminates.

Thus, certain non-limiting embodiments of the method 600 allow determining a configuration of the aligner 20 causing the lower arch form 10 of the subject to move to and remain in the desired position relative to the upper arch form 11 using specifics of the subject's intraoral anatomy, such as the topography of the current occlusion between the lower and upper teeth 12, 13. This may allow improving the wear comfort of the aligner 20 in the course of the orthodontic treatment, which may thus increase efficacy thereof.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to providing examples of implementations of the present technology rather than being limiting. The scope of the present technology is therefore intended to be limited solely by the scope of the appended claims.

The invention claimed is:

1. A method for making an orthodontic appliance for a subject, the method comprising:

obtaining a 3D digital model comprising a plurality of vertices representative of surfaces of an upper arch form and a lower arch form of the subject, the upper arch form including upper teeth and the lower arch form including lower teeth, each one of the upper teeth and the lower teeth having a respective occlusal surface portion defining a current occlusion therebetween;

obtaining an indication of a desired occlusion between the upper and lower arch forms;

determining based on the desired occlusion, a shift value between the current occlusion and the desired occlusion;

generating based on the desired occlusion, an appliance 3D digital model of the orthodontic appliance, such that:
an outer surface of the appliance 3D digital model corresponds to the respective occlusal surface portion of the given one of the upper and lower teeth having been repositioned towards the desired occlusion by the shift value,
the generating comprising generating an occlusal surface 3D digital model representative of a topography of the current occlusion between the upper and lower teeth by:
identifying, in the 3D digital model, for each vertex defining the respective occlusal surface of one of the upper teeth and the lower teeth, a corresponding vertex in the respective occlusal surface of the other one of the upper and lower teeth, thereby identifying pairs of vertices between the respective occlusal surfaces of the upper and lower teeth; and
determining a given vertex defining the occlusal surface 3D digital model as being a point between a given one of the pairs of vertices; and
causing manufacture of the orthodontic appliance based on the appliance 3D digital model.

2. The method of claim 1, wherein
the occlusal surface 3D digital model has at least one occlusal surface landmark aligning with one or both of:
a corresponding upper teeth landmark in the respective occlusal surface portion of the upper teeth and a lower teeth landmark in the respective occlusal surface portion of the lower teeth; and
wherein the generating the occlusal surface 3D digital model further comprises applying, in the 3D digital model, the occlusal surface 3D digital model to one or both of the respective occlusal surface portions of the upper teeth and the respective occlusal surface portion of the lower teeth, the applying comprising:
positioning, in the 3D digital model, the occlusal surface 3D digital model on one of (i) the respective occlusal surface portion of the upper teeth such that the landmark aligns with the upper teeth landmark, and (ii) the respective occlusal surface portion of the lower teeth such that the landmark aligns with the lower teeth landmark; and
moving the occlusal surface 3D digital model towards the desired occlusion; and
generating the appliance 3D digital model based on the 3D digital model with the occlusal surface 3D digital model applied thereon.

3. The method of claim 1, wherein the determining the shift value comprises obtaining data indicative of the current occlusion and the desired occlusion of the upper arch form and the lower arch form, and identifying a distance value, along a translational direction, between the current occlusion and the desired occlusion.

4. The method of claim 3, wherein the translational direction is determined along an occlusal plane between the upper and lower teeth.

5. The method of claim 3, further comprising generating, based on the shift value, a plurality of shift intervals, and wherein the moving the occlusal surface 3D digital model by the shift value comprises moving the occlusal surface 3D digital model by a given one of the shift intervals.

6. The method of claim 5, wherein the orthodontic appliance is a one of a plurality of orthodontic appliances to be applied to the subject during an orthodontic treatment, a given one of the plurality of orthodontic appliances being determined based on a respective appliance 3D digital model with the occlusal surface 3D digital model being moved to a respective one of the plurality of shift intervals.

7. The method of claim 5, wherein each one of the plurality of shift intervals is equal.

8. The method of claim 1, further comprising identifying each vertex defining the respective occlusal surface of one of the upper teeth and the lower teeth by:
positioning an occlusal plane between the upper teeth and the lower teeth; and
translating vertices from the occlusal plane to one of the upper teeth and the lower teeth, and determining the translated vertices as vertices defining the respective occlusal surface.

9. The method of claim 8, wherein the translating the vertices comprises moving the vertices along normal vectors from the occlusal plane towards the one of the upper teeth and the lower teeth.

10. The method of claim 1, wherein the determining the given vertex defining the occlusal surface 3D digital model comprises determining a point between the given one of the pairs of vertices which is a predetermined distance between the given one of the pairs of vertices.

11. The method of claim 1, wherein the identifying the corresponding vertex, for a given vertex defining the respective occlusal surface of one of the upper teeth and the lower teeth, comprises extending therefrom a line towards the other of the upper teeth and the lower teeth.

12. The method of claim 11, wherein the line is defined as one of: (i) extending parallel to an axis of a given tooth associated with the given vertex, (ii) extending along a movement trajectory of the upper arch form relative to the lower arch form when moving from the current occlusion to the desired occlusion, and (iii) extending along a normal vector to a surface of the given tooth associated with the given vertex.

13. The method of claim 1, further comprising identifying vertices in which a distance between the pair of vertices is greater than a predetermined distance threshold value, and removing the vertices in which the distance between the pair of vertices is greater than the predetermined distance threshold value from at least one of the respective occlusal surfaces of the upper teeth and the lower teeth of the 3D digital model.

14. The method of claim 2, further comprising smoothing the occlusal surface 3D digital model.

15. The method of claim 1, wherein the manufacture of the orthodontic appliance is by additive manufacturing, and the causing comprises sending instructions to an additive manufacturing system.

16. The method of claim 1, wherein the generating comprises:
obtaining a raw appliance 3D digital model having been determined based on the 3D digital model such that:
both an inner surface and an outer surface of the raw appliance 3D digital model correspond to the respective occlusal surface portion of the given one of the upper and lower teeth in the current occlusion therebetween;
determining using the 3D digital model, an occlusal surface 3D digital model representative of a topography of the current occlusion between the upper arch form and the lower arch form,
the occlusal surface 3D digital model having at least one occlusal surface landmark aligning with one or both of: a corresponding upper teeth landmark in the respective occlusal surface portion of the upper teeth and a lower teeth landmark in the respective occlusal surface portion of the lower teeth;

applying to the outer surface of the raw appliance 3D digital model, the occlusal surface 3D digital model, the applying comprising:

positioning, in the raw appliance 3D digital model, the occlusal surface 3D digital model on the respective occlusal surface portion of the given one of the upper teeth and the lower teeth such that the corresponding landmark aligns with a respective one of the upper teeth landmark and the lower teeth landmark; and moving the occlusal surface 3D digital model towards the desired occlusion; and determining the appliance 3D digital model as being the raw appliance 3D digital model with the occlusal surface 3D digital model applied thereon.

17. A system for making an orthodontic appliance for a subject, the system comprising at least one processor and at least one non-transitory computer-readable medium comprising executable instructions that, when executed by the at least one processor, cause the system to:

obtain a 3D digital model comprising a plurality of vertices representative of surfaces of an upper arch form and a lower arch form of the subject, the upper arch form including upper teeth and the lower arch form including lower teeth, each one of the upper teeth and the lower teeth having a respective occlusal surface portion defining a current occlusion therebetween;

obtain an indication of a desired occlusion between the upper and lower arch forms;

determine, based on the desired occlusion, a shift value between the current occlusion and the desired occlusion;

generate, based on the desired occlusion, an appliance 3D digital model of the orthodontic appliance, such that:

an outer surface of the appliance 3D digital model corresponds to the respective occlusal surface portion of the given one of the upper and lower teeth having been repositioned towards the desired occlusion by the shift value, generating comprising generating an occlusal surface 3D digital model representative of a topography of the current occlusion between the upper and lower teeth by:

identifying, in the 3D digital model, for each vertex defining the respective occlusal surface of one of the upper teeth and the lower teeth, a corresponding vertex in the respective occlusal surface of the other one of the upper and lower teeth, thereby identifying pairs of vertices between the respective occlusal surfaces of the upper and lower teeth; and determining a given vertex defining the occlusal surface 3D digital model as being a point between a given one of the pairs of vertices; and cause manufacture of the orthodontic appliance based on the appliance 3D digital model.

* * * * *